US012180497B2

(12) United States Patent
Liu et al.

(10) Patent No.: US 12,180,497 B2
(45) Date of Patent: Dec. 31, 2024

(54) RESISTANCE GENES ASSOCIATED WITH DISEASE RESISTANCE IN SOYBEANS

(71) Applicant: Syngenta Crop Protection AG, Basel (CH)

(72) Inventors: Qingli Liu, Durham, NC (US); Robert Arthur Dietrich, Durham, NC (US); Thomas Joseph Curley, Jr., Durham, NC (US); Becky Welsh Breitinger, Durham, NC (US); John Daniel Hipskind, Durham, NC (US); John Luther Dawson, Durham, NC (US); Xiaoping Tan, Durham, NC (US); Andrew David Farmer, Santa Fe, NM (US)

(73) Assignee: Syngenta Crop Protection AG, Basel (CH)

( * ) Notice: Subject to any disclaimer, the term of this patent is extended or adjusted under 35 U.S.C. 154(b) by 39 days.

(21) Appl. No.: 17/631,174

(22) PCT Filed: Jul. 30, 2020

(86) PCT No.: PCT/US2020/044221

§ 371 (c)(1),
(2) Date: Jan. 28, 2022

(87) PCT Pub. No.: WO2021/022022

PCT Pub. Date: Feb. 4, 2021

(65) Prior Publication Data

US 2022/0267789 A1 Aug. 25, 2022

Related U.S. Application Data

(60) Provisional application No. 62/881,881, filed on Aug. 1, 2019.

(51) Int. Cl.

| | |
|---|---|
| ***C12N 15/82*** | (2006.01) |
| ***A01H 1/00*** | (2006.01) |
| ***A01H 1/04*** | (2006.01) |
| ***A01H 5/10*** | (2018.01) |
| ***A01H 6/54*** | (2018.01) |

(52) U.S. Cl.
CPC ......... *C12N 15/8282* (2013.01); *A01H 1/045* (2021.01); *A01H 1/1255* (2021.01); *A01H 5/10* (2013.01); *A01H 6/542* (2018.05)

(58) Field of Classification Search
None
See application file for complete search history.

(56) References Cited

U.S. PATENT DOCUMENTS

| | | | |
|---|---|---|---|
| 2009/0093620 | A1 | 4/2009 | Kovalic et al. |
| 2017/0273260 | A1 | 9/2017 | Baley et al. |
| 2018/0255733 | A1 | 9/2018 | Lee et al. |

FOREIGN PATENT DOCUMENTS

| | | |
|---|---|---|
| WO | 2019/13918 A1 | 5/2019 |

OTHER PUBLICATIONS

International Search Report for International Application No. PCT/US2020/044221 mailed Nov. 18, 2020.
Periyannan et al., "An overview of genetic rust resistance: From broad to specific mechanisms," PLoS Pathogens, Jul. 13, 2017 (Jul. 13, 2017), vol. 13, Issue 7, pp. 1-6.

*Primary Examiner* — Medina A Ibrahim
(74) *Attorney, Agent, or Firm* — Suparna Kanjilal

(57) ABSTRACT

The present invention relates to methods and compositions for identifying, selecting and/or producing a Disease resistant soybean plant or germplasm using genes derived from *Glycine canescens, Glycine clandestina, Glycine tomentella*. A soybean plant or germplasm that has been identified, selected and/or produced by any of the methods of the present invention is also provided. Disease resistant soybean seeds, plants and germplasms are also provided.

37 Claims, 16 Drawing Sheets

Specification includes a Sequence Listing.

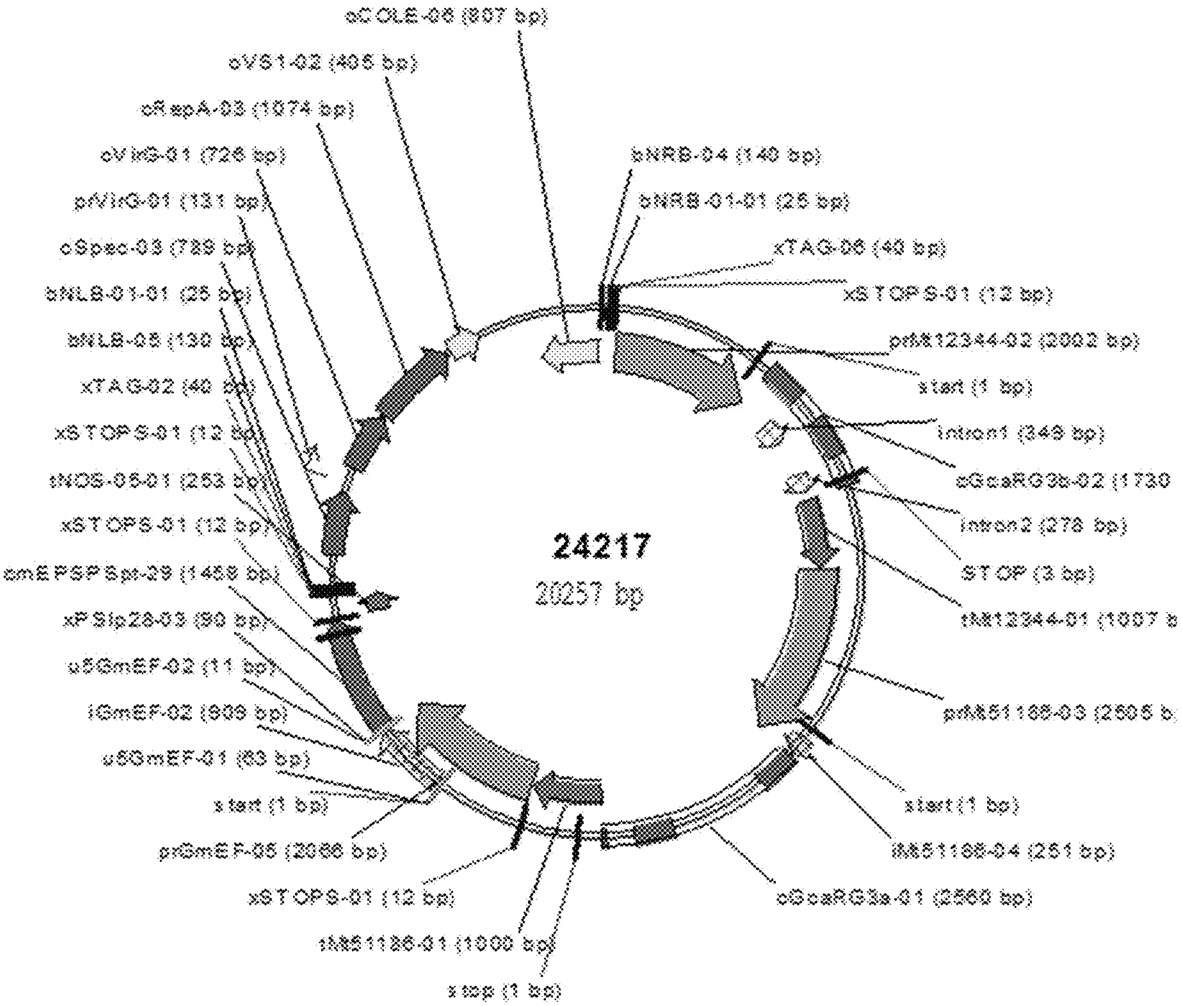
Figure 1: Illustration of binary vector 24217.

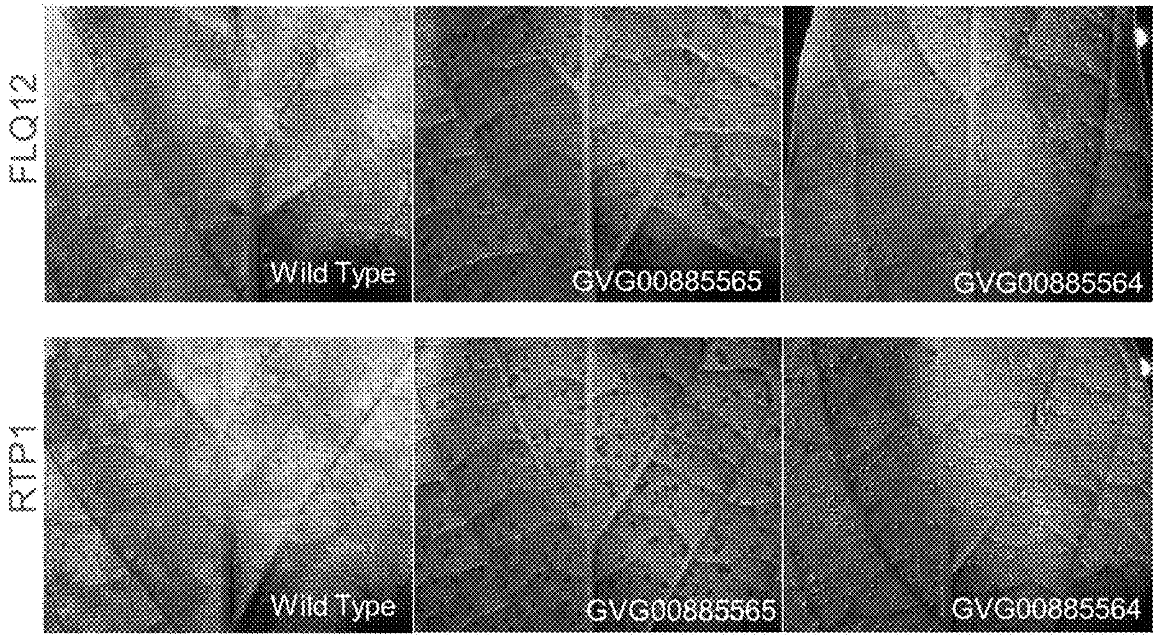
FIGURE 2. Photographs of rust bioassay experiments conducted on leaves collected from primary soybean events generated from binary vector 24217.

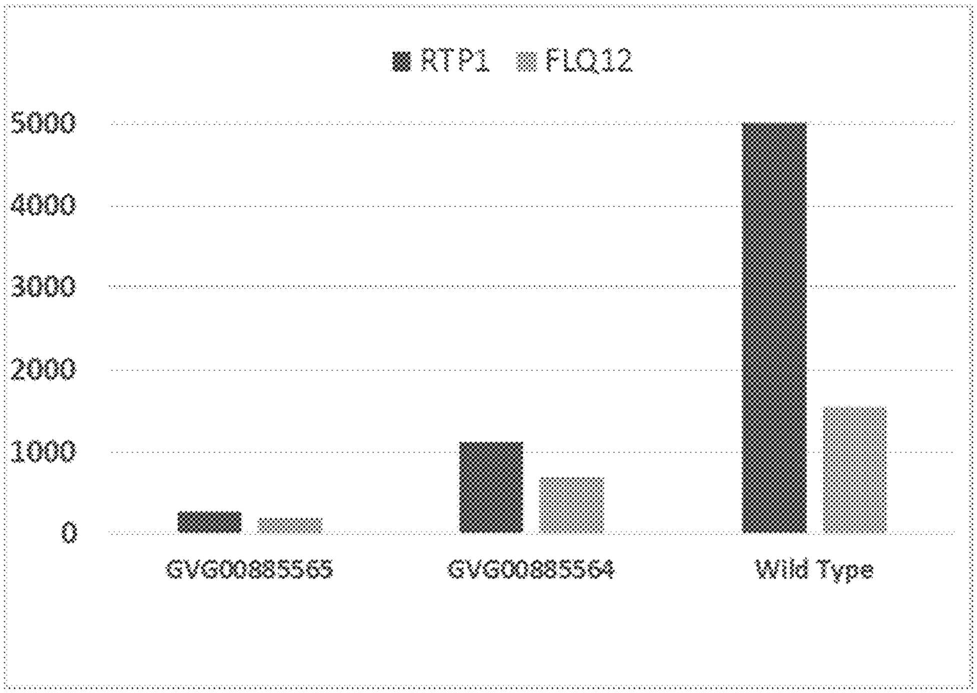
Figure 3. Relative expression (y-axis) of soybean rust β-tubulin gene in construct 24217 primary soybean events at 14 days post inoculation.

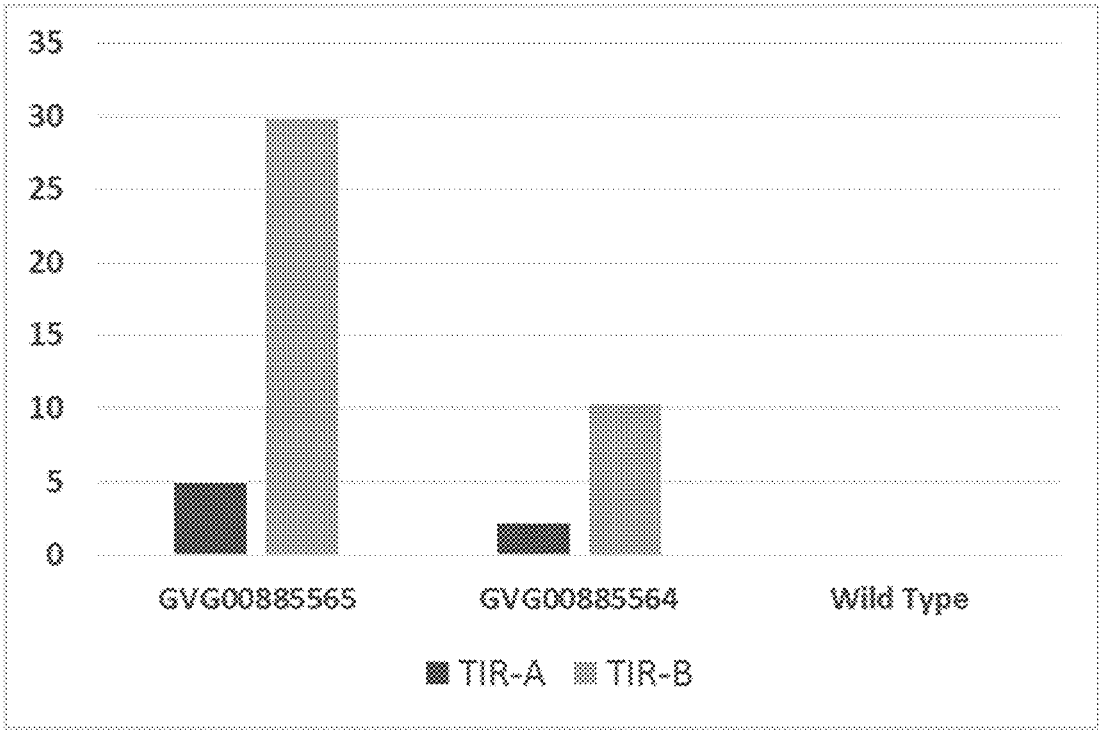
**Figure 4. Relative expression (y-axis) of *G. canescens TIR-A* and *TIR-B* genes in transgenic soybean events conferring resistance to soybean rust.**

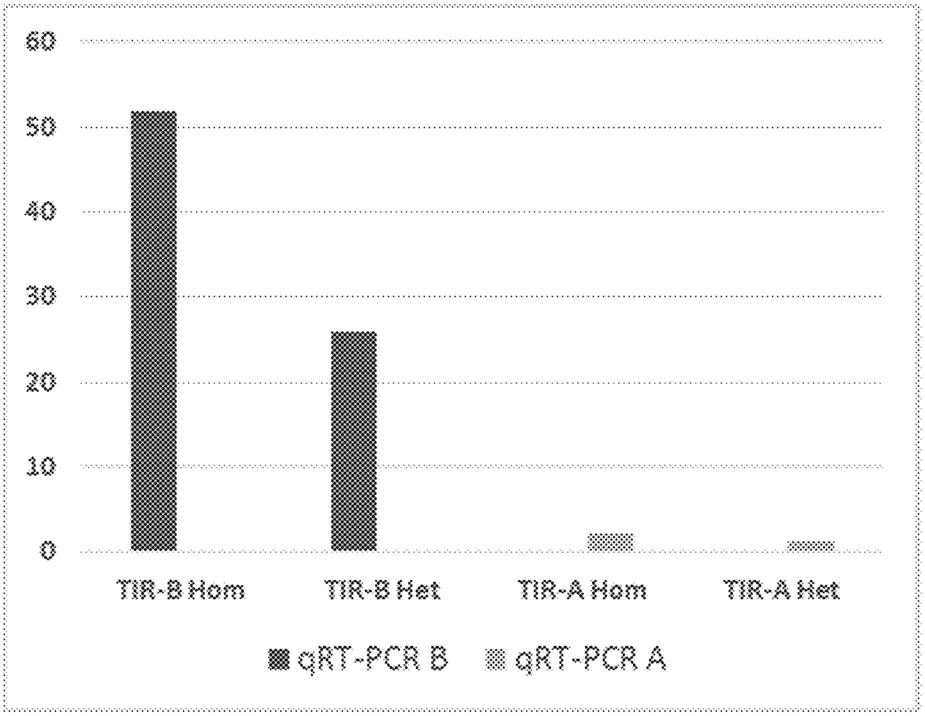
**Figure 5. Summary of qRT-PCR analysis of GVG00885565 T1 – generation plants that are homozygous or heterozygous for *TIR-A* and *TIR-B* genes.**

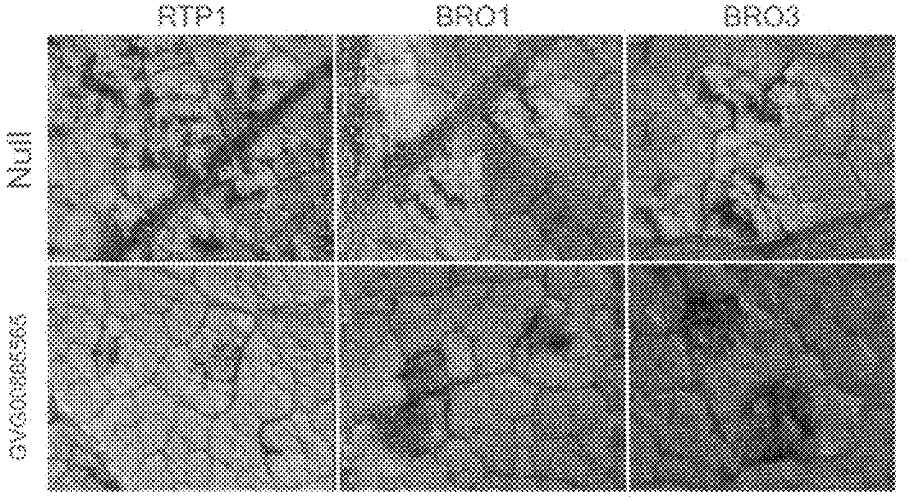
Figure 6. The T1-generation null and homozygous GVG00885565 plants 14 days post-inoculation with three different soybean rust populations. Note the high degree of rust sporulation on the leaves of null plants.

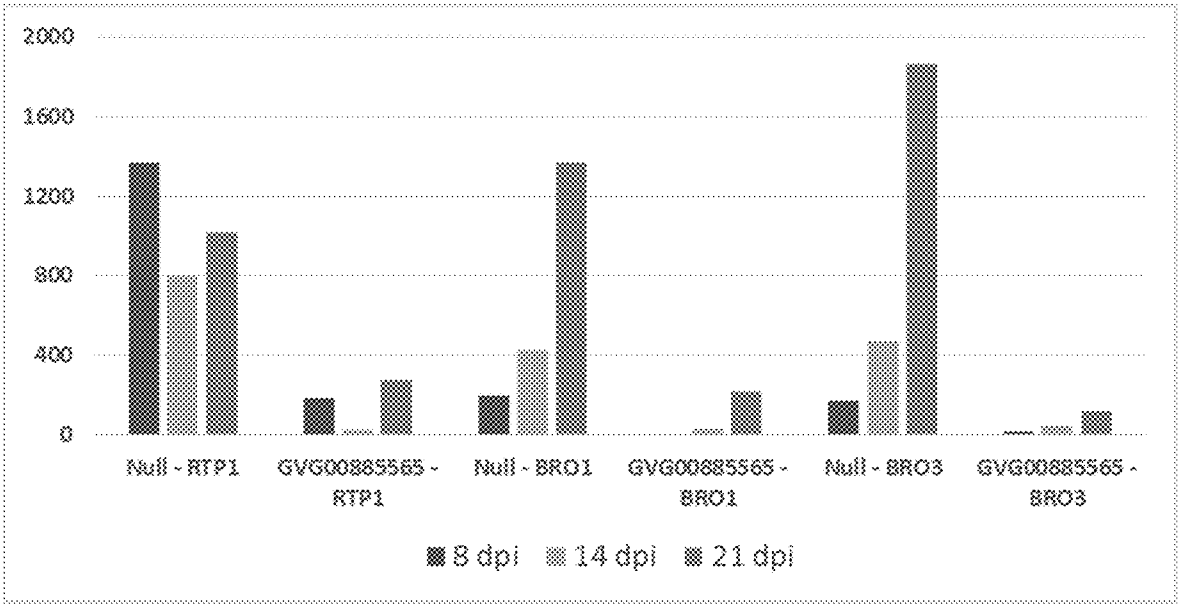
**Figure 7. The relative expression (y-axis) of soybean rust β-tubulin gene at 8, 14 and 21 days post-inoculation in the null and *TIR-A, TIR-B* homozygous plants.**

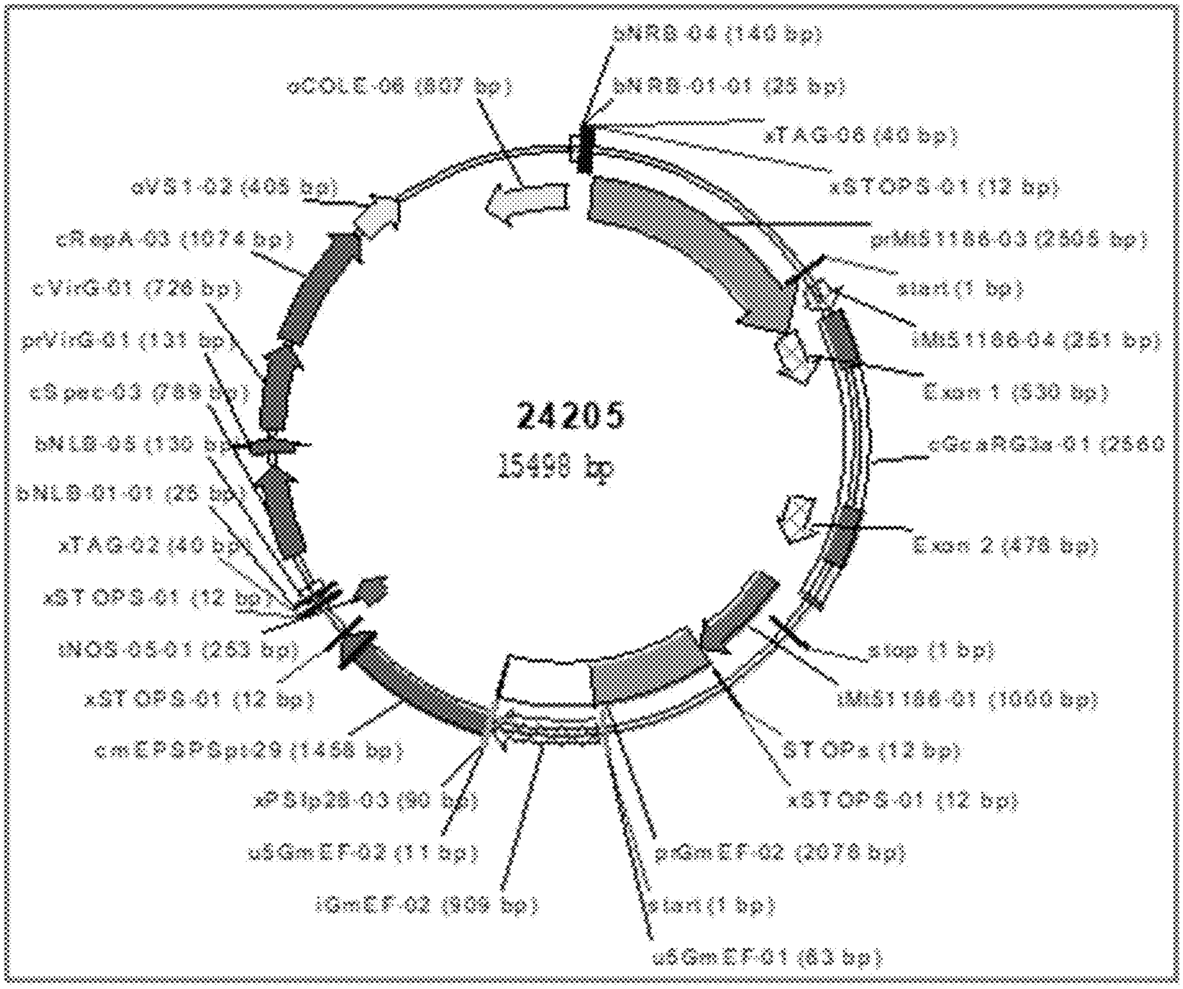
Figure 8A. Binary vector map of *TIR-A* (24205) used in co-transformation experiments.

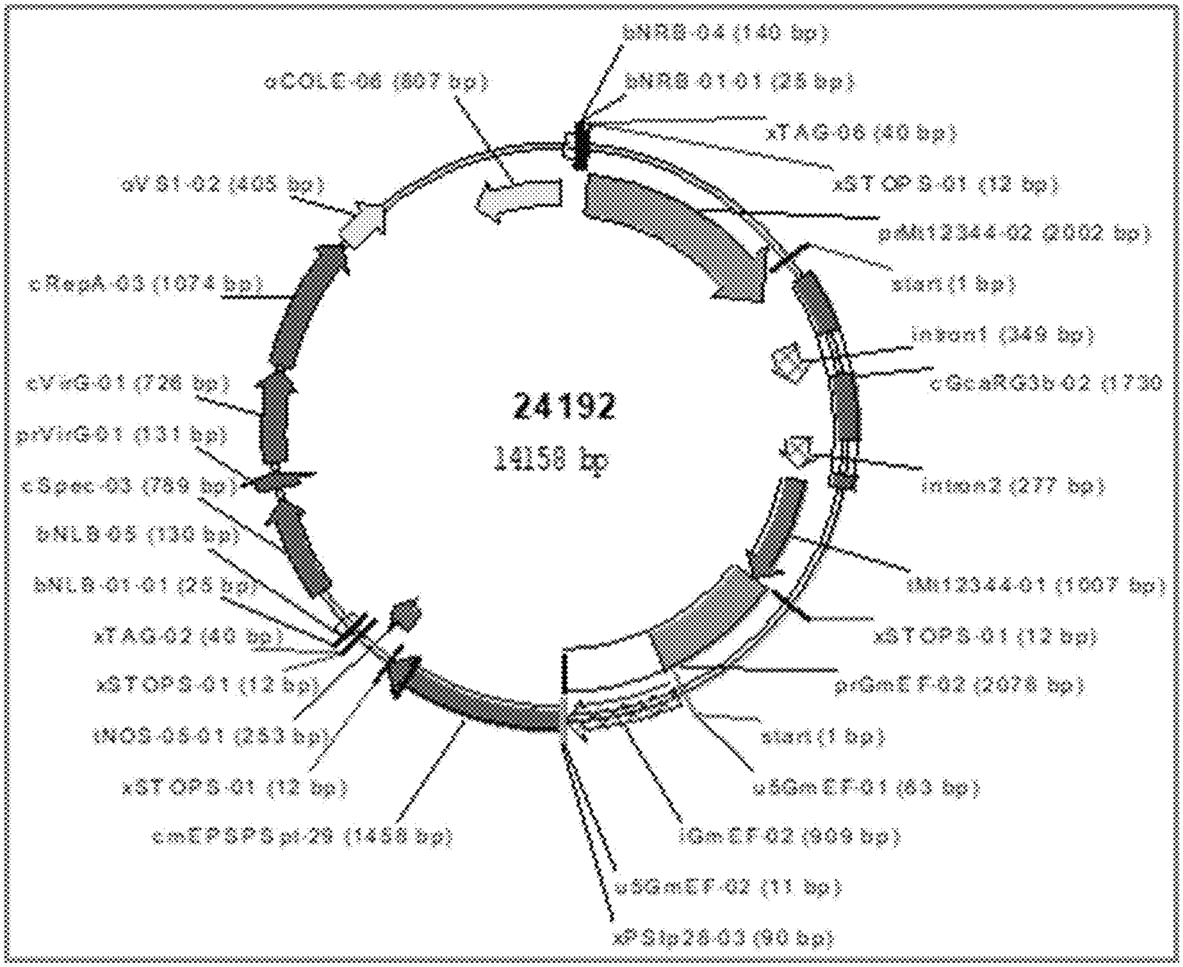
Figure 8B. **Binary vector maps of *TIR-B* (24192) used in co-transformation experiments.**

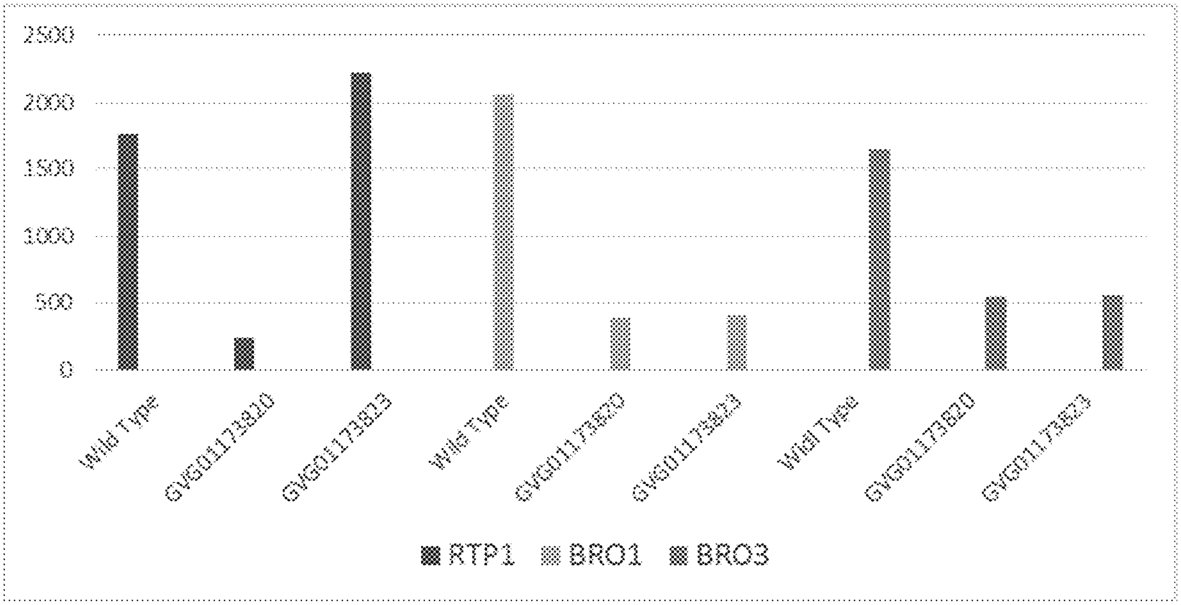
Figure 9: Summary of qRT-PCR relative expression of soybean rust β-tubulin gene expression (y-axis) from primary soybean events at 14 days post inoculation.

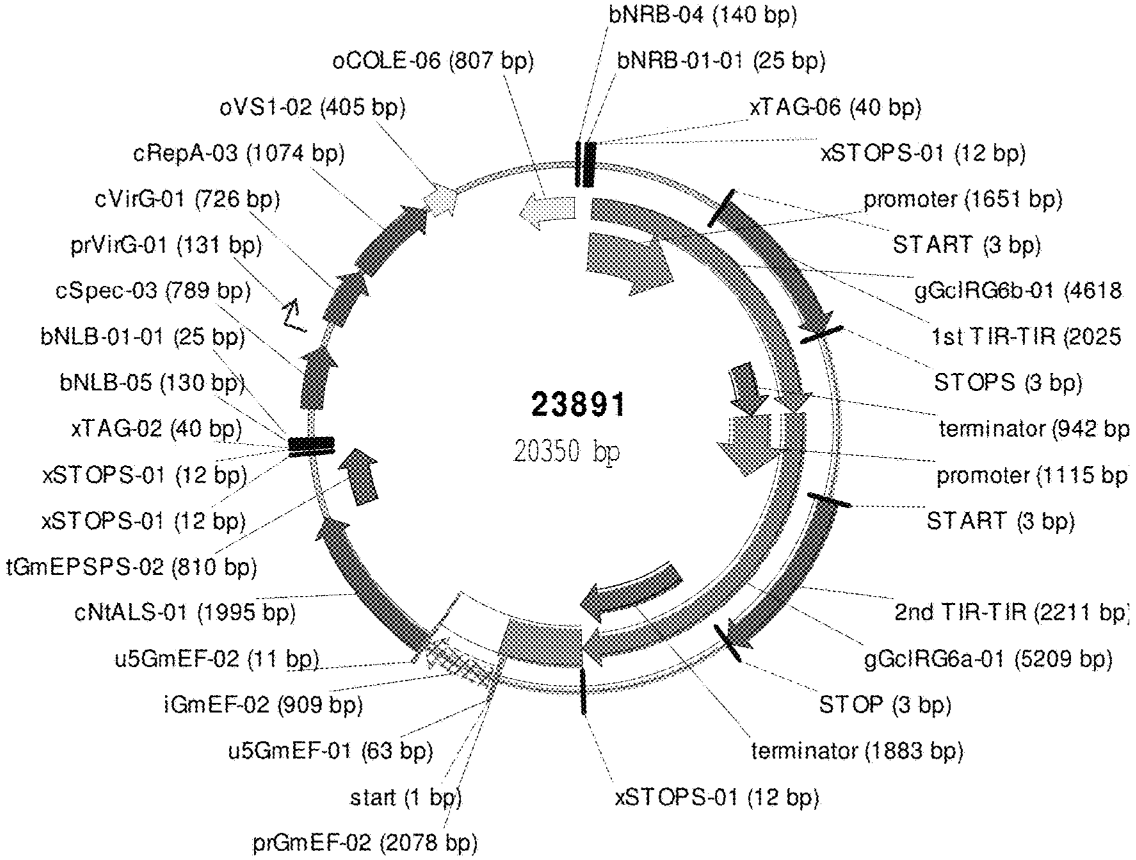
Figure 10. Illustration of binary vector 23891; G. clandestina PI339656 – TIR-A and TIR-B

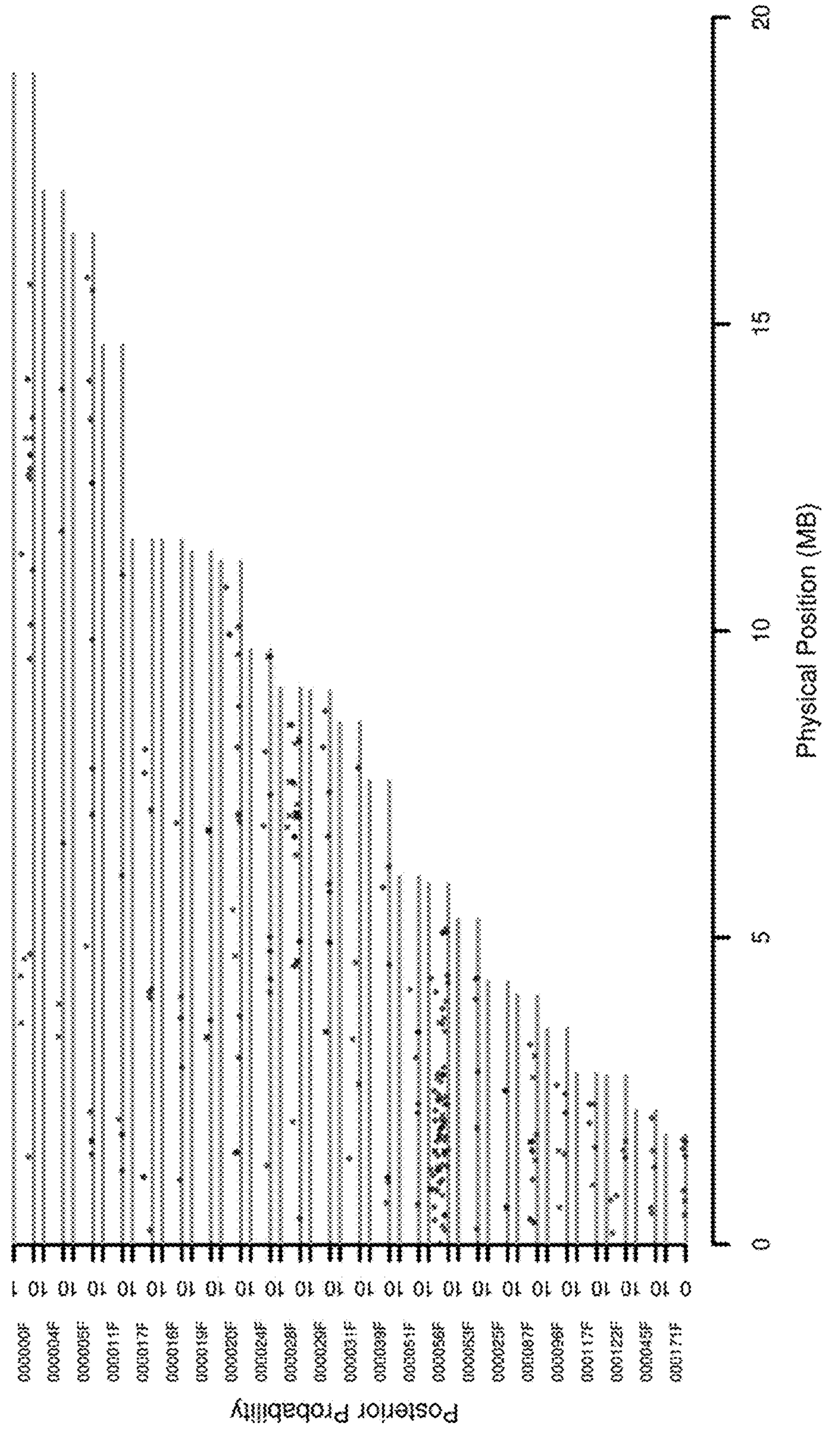
**FIG. 11: Depiction of *Glycine canescens* PI440935 SNPs Associated with ASR Resistance (i.e. each dot equals 1 SNP that associates with ASR resistanc**

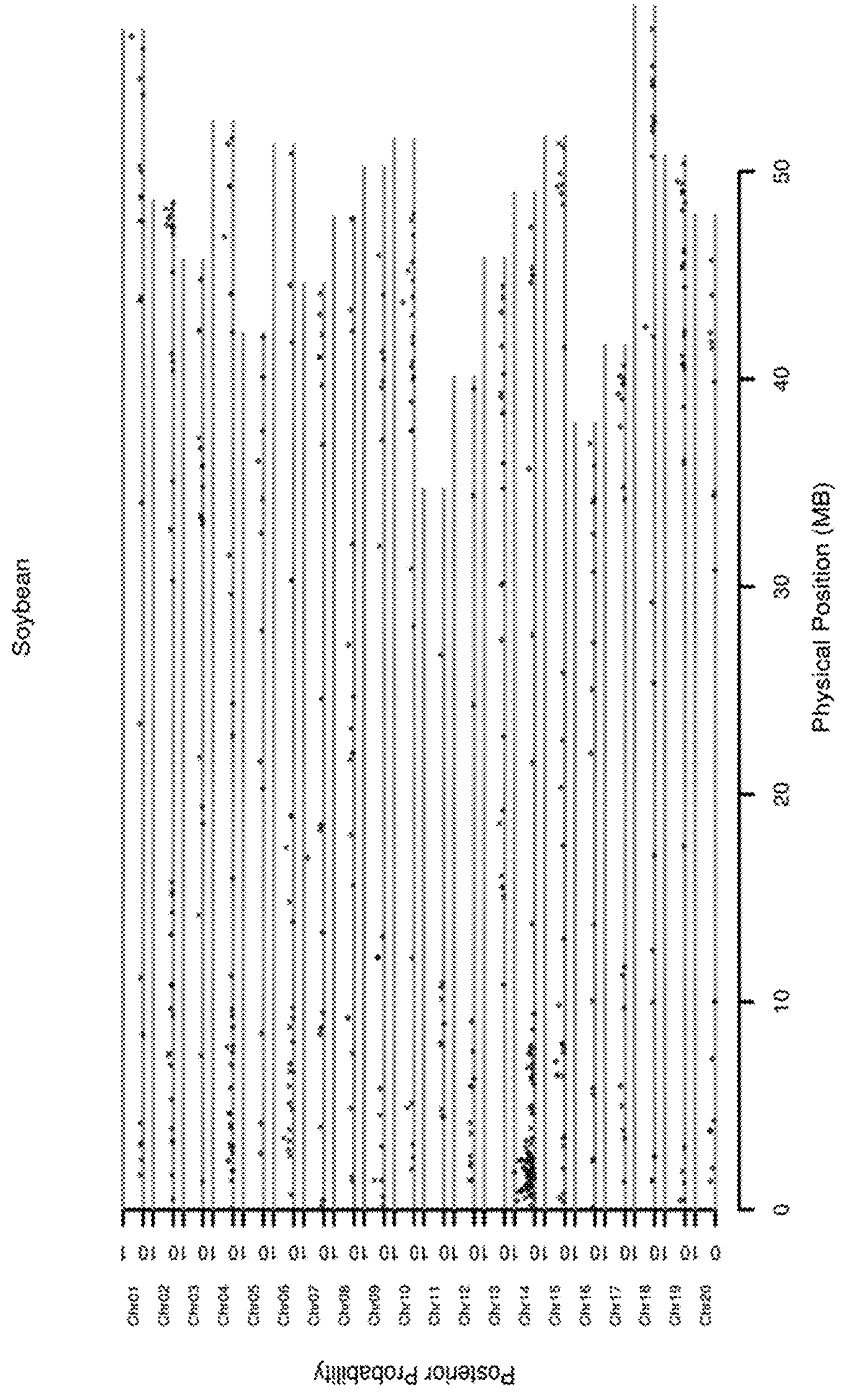
**FIG. 12: Depiction of *Glycine canescens* PI440935 SNPs Associated with ASR Resistance with chromosome number (i.e. each dot equals 1 SNP that associates with ASR resistance)**

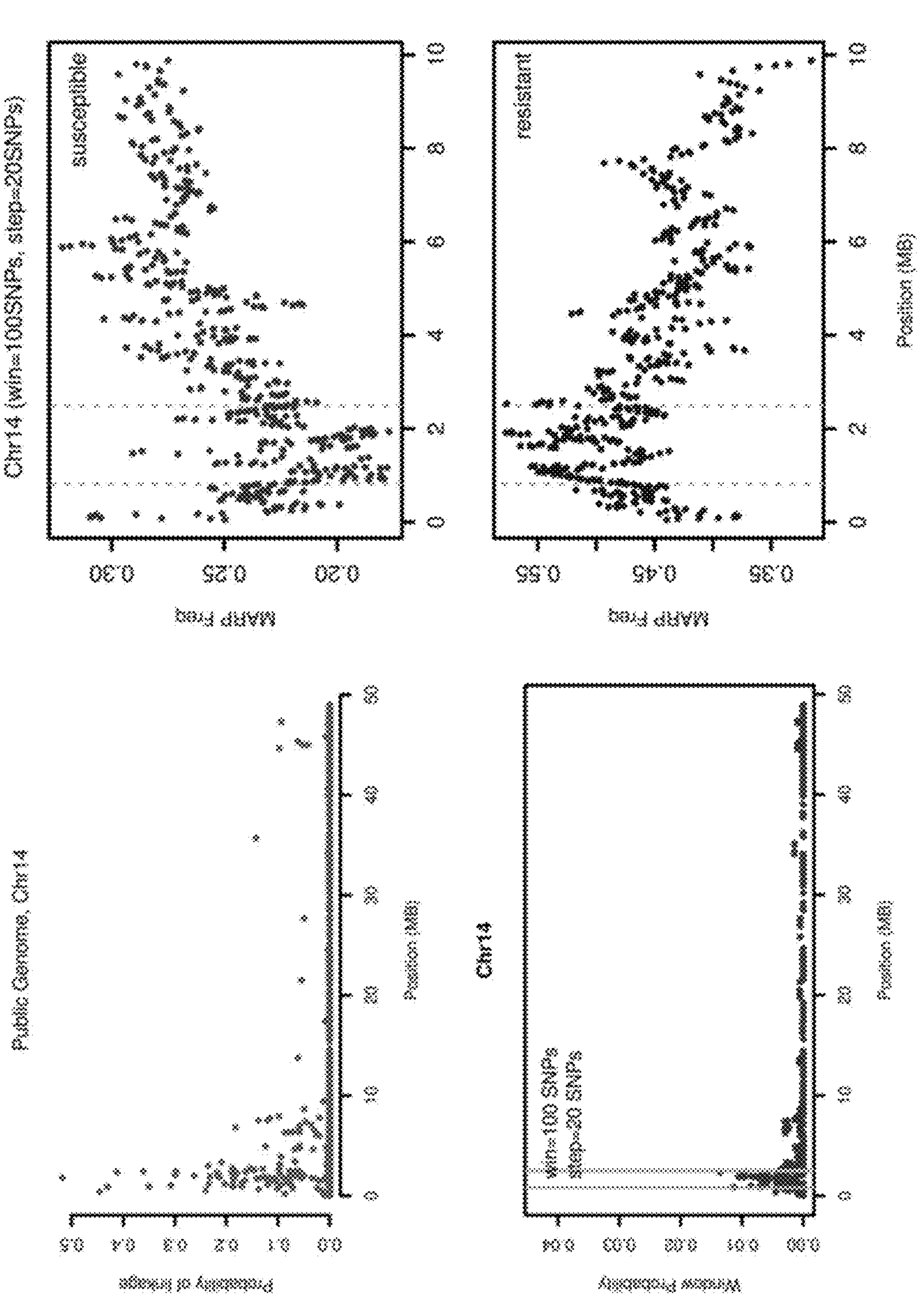
FIG. 13: Mapping Interval Discovery for Scaffold 000056F (Suggested interval Chromosome 14 0.85 – 2.5 Mb

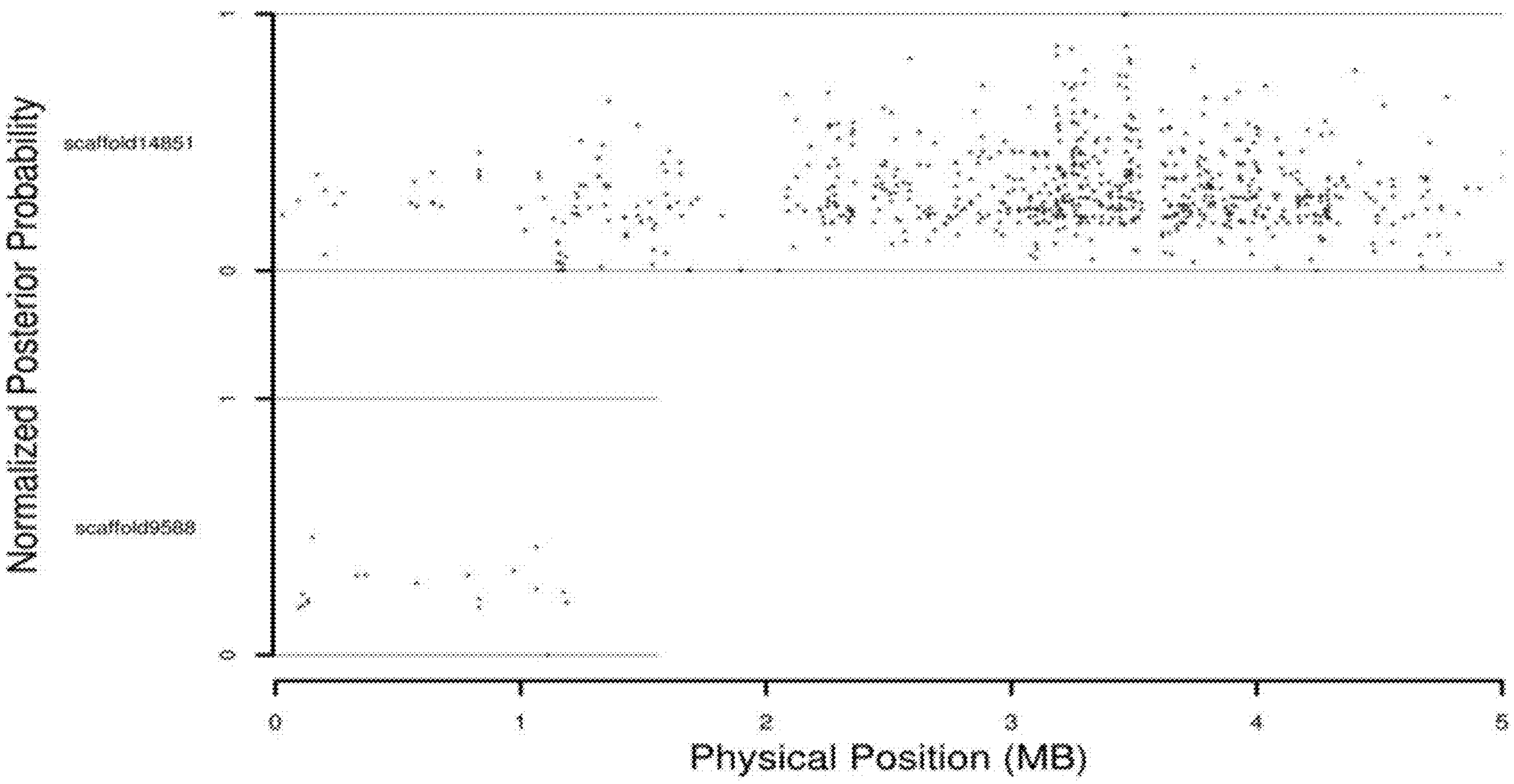
**FIG. 14: Depiction of *Glycine clandestina* PI339656 SNPs Associated with ASR Resistance (i.e. each dot equals 1 SNP that associates with ASR resistance; scaffold 14851 (Chr14) & scaffold 9588 (CHR9))**
InformativeSNPs = 10,915, Total SNPs on Top Contigs = 2,165

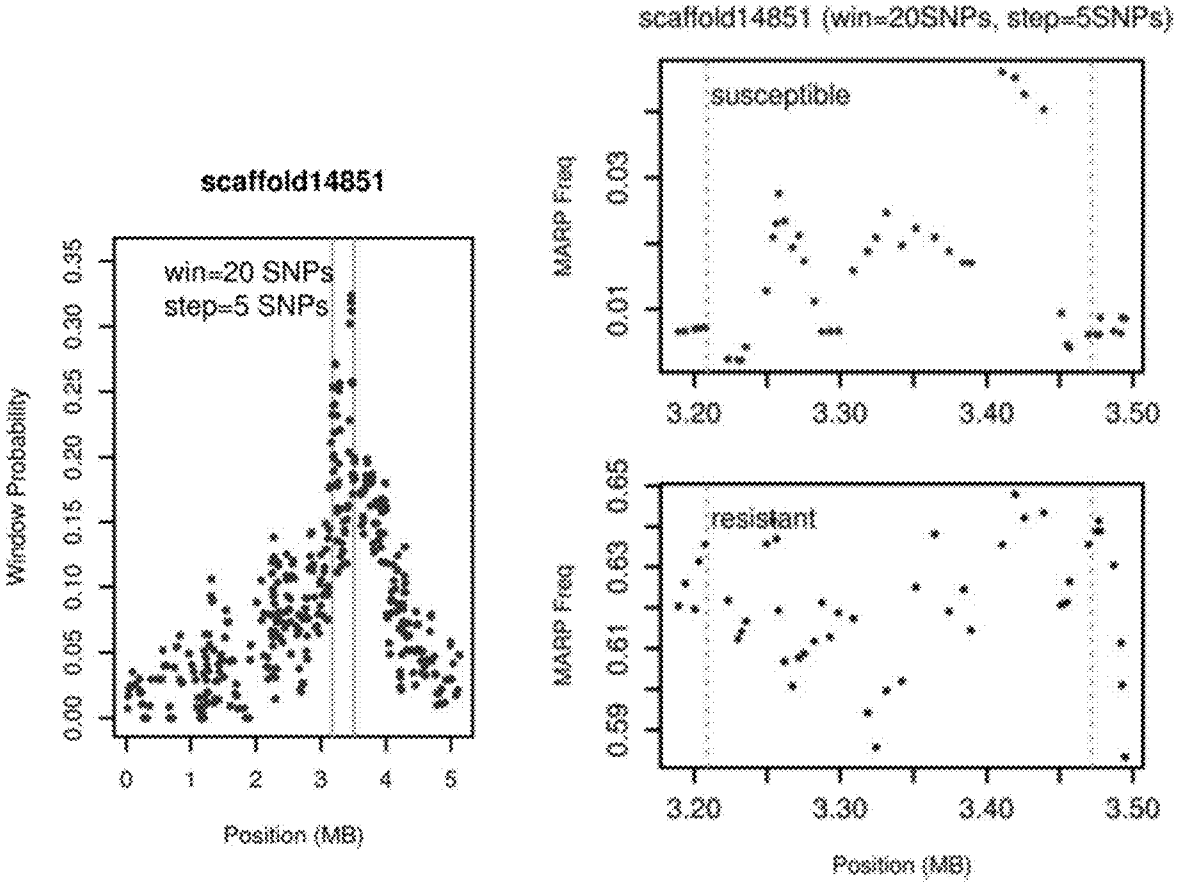
FIG. 15: Mapping Interval Discovery for Scaffold 14851 (Suggested interval Chromosome 14: 3.18-3.5Mb)

RESISTANCE GENES ASSOCIATED WITH DISEASE RESISTANCE IN SOYBEANS

RELATED APPLICATION INFORMATION

This application is a 371 of International Application No. PCT/US2020/044221, filed 30 Jul. 2020, which claims priority to 62/881,881, filed 1 Aug. 2019, the contents of which are incorporated herein by reference herein.

STATEMENT REGARDING ELECTRONIC SUBMISSION OF A SEQUENCE LISTING

A Sequence Listing in ASCII text format, submitted under 37 C.F.R. § 1.821, entitled "81819-US-REG-ORG-P-1-SequenceList_ST25.txt", 24.0 MB (25,265,401 bytes) in size, generated on Aug. 1, 2019 and filed via EFS-Web is provided in lieu of a paper copy. This Sequence Listing is hereby incorporated by reference into the specification for its disclosures.

FIELD OF THE INVENTION

The present invention relates to compositions and methods for identifying, selecting and producing enhanced disease and/or pathogen resistant plants using novel resistance genes.

STATEMENT REGARDING ELECTRONIC SUBMISSION OF A SEQUENCE LISTING

A Sequence Listing in ASCII text format, submitted under 37 C.F.R. § 1.821, entitled "81819-WO-REG-ORG-P-1-SequenceList_ST25" generated on 1 Aug. 2019 and filed via EFS-Web is provided in lieu of a paper copy. This Sequence Listing is hereby incorporated by reference into the specification for its disclosures.

BACKGROUND

Plant pathogens are known to cause considerable damage to important crops, resulting in significant agricultural losses with widespread consequences for both the food supply and other industries that rely on plant materials. As such, applicant desires to reduce the incidence and/or impact of agricultural pathogens on crop production.

Several pathogens have been associated with damage to soybeans, which individually and collectively have the potential to cause significant yield losses in the United States and throughout the world. Exemplary pathogens include, but are not limited to fungi (e.g., genus *Phytophthora* and Asian Soybean rust *Phakopsora pachyrhizi*), nematodes (e.g., genus *Meloidogyne*, particularly, *Meloidogyne javanica*), and soybean stem canker. Given the significant threat to global food supplies that these pathogens present as well as the time and expense associated with treating soybean crops to prevent yield loss, new methods for producing pathogen resistant soybean cultivars are needed. What is needed is novel resistance genes (herein, "R-Genes") that can be introduced into commercial soybean plants to control soybean pathogens.

SUMMARY OF THE INVENTION

This summary lists several embodiments of the presently disclosed subject matter, including variations of these embodiments.

Compositions and methods for identifying, selecting and producing *Glycine* plants (including wild Glycines (e.g. *Glycine canescens, Glycine clandestina, Glycine tomentella*), elite *Glycine* lines and *Glycine max* lines) with enhanced disease resistance are provided. Disease resistant soybean plants and germplasms are also provided. In some embodiments, methods of producing a disease resistant soybean plant are provided.

In one aspect of the invention there is provided a DNA construct that comprises a promoter that functions in plant cells operably linked to a novel resistance gene (herein an R-Gene). In another aspect of the invention there is provided a transgenic plant that contains the DNA construct and has increased expression of the R-gene, wherein the transgenic plant is resistant to soybean pathogens, particularly Asian Soybean Rust.

In another aspect of the invention is a method of preparing a fertile transgenic plant comprising providing a plant expression cassette comprising an R-Gene and contacting recipient plant cells with the plant expression cassette under conditions permitting the uptake of the plant expression cassette by the recipient cells; selecting the recipient plant cells that contain the plant expression cassette; regenerating plants from the selected recipient plant cells; and identifying a fertile transgenic plant that is resistant to soybean pathogens, particularly Asian Soybean Rust (herein "ASR").

In another aspect of the invention there is provided a fertile transgenic plant that comprises a plant expression cassette comprising an R-Gene, wherein the plant has increased expression levels of the R-gene, and wherein the plant is resistant to soybean pathogens, particularly Asian Soybean Rust. In one aspect of the invention, the plant is an elite soybean plant that is resistant to soybean pathogens.

In another aspect of the invention there is provided a method of controlling ASR in a field comprising the step of planting the seed from a plant comprising an R-gene of the invention.

Thus, it is an object of the presently disclosed subject matter to provide methods for conveying pathogen resistance into non-resistant soybean germplasm or plant lines.

Further the presently disclosed subject matter provides novel *Glycine max* lines comprising in its genome a R-gene that is derived from a wild glycine species, e.g. *Glycine canescens* or *Glycine clandestina* or *Glycine tomentella*, and further confers ASR resistance in the novel *Glycine max* line. Soybean plants and/or germplasms identified, produced or selected by the methods of this invention are also provided, as are any progeny and/or seeds derived from a soybean plant or germplasm identified, produced or selected by these methods.

As still a further aspect, the invention encompasses transgenic plants comprising a plant cell, plant part, nucleotide sequence, expression cassette, vector and/or R-genes of the invention.

As a further aspect are seeds that produce the transgenic plants of the invention and seeds produced by the transgenic plants of the invention.

Also provided are harvested products derived from the transgenic plants of the invention, wherein the harvested product optionally comprises a nucleotide sequence, expression cassette, vector and/or R-gene of the invention. Further provided are processed products derived from the harvested products of the invention, wherein the harvested product optionally comprises a nucleotide sequence, expression cassette, vector and/or R-gene of the invention.

Still further, the invention provides as an additional aspect a method of producing a transgenic plant with increased resistance to a soybean pathogen. In embodiments, the method comprises introducing into a plant a polynucleotide, expression cassette, or vector of the invention, wherein the R-gene is expressed in the plant, thereby producing a transgenic plant with increased resistance to a soybean pathogen. Optionally, the introducing step comprises: (i) transforming a plant cell with the polynucleotide, expression cassette or vector and regenerating a transgenic plant; or (ii) crossing a first plant comprising the polynucleotide, expression cassette or vector with a second plant. In embodiments, the method further comprises producing a seed from the transgenic plant. In embodiments, the method further comprises obtaining a progeny plant from the transgenic plant, wherein the progeny plant comprises the polynucleotide, the expression cassette or the vector, expresses the R-gene and has increased resistance to a soybean pathogen.

As yet another aspect, the invention provides a method of producing a transgenic plant with increased resistance to a soybean plant pathogen (e.g., Asian Soybean Rust), the method comprising: (a) planting a seed comprising a polynucleotide, expression cassette or vector of the invention; and (b) growing a transgenic plant from the seed, wherein the transgenic plant comprises the polynucleotide, expression cassette or vector and produces the R-gene and has increased resistance to a soybean pathogen. In embodiments, the method further comprises: (c) harvesting a seed from the transgenic plant of (b), wherein the harvested seed comprises the polynucleotide, expression cassette, vector and/or the R-gene.

Still further, as another aspect, the invention provides a method of producing a seed. In embodiments, the method comprises: (a) providing a transgenic plant that comprises a polynucleotide, expression cassette or vector of the invention; and (b) harvesting a seed from the transgenic plant of (a), wherein the harvested seed comprises the polynucleotide, expression cassette or vector and/or a R-gene of the invention.

The invention further contemplates a method of producing a hybrid plant seed. In representative embodiments, the method comprises: (a) crossing a first inbred plant, which is a transgenic plant comprising a polynucleotide, expression cassette or vector of the invention with a second, different inbred plant, which may or may not comprise the polynucleotide, expression cassette or vector of the invention; and (b) harvesting hybrid seed from a progeny plant.

The invention is also drawn to methods of using the polynucleotides of the invention, for example, in DNA constructs or expression cassettes or vectors for transformation and expression in organisms, including plants. The nucleotide or amino acid sequences may be native or synthetic sequences that have been designed for expression in an organism such as a plant.

In embodiments, the invention provides a method of using a polynucleotide, expression cassette or vector of the invention to produce a transgenic seed, where the transgenic seed grows a transgenic plant with increased resistance to a soybean pathogen.

The foregoing and other objects and aspects of the present invention are explained in detail in the drawings and specification set forth below.

BRIEF DESCRIPTION OF THE DRAWINGS

FIG. 1 is an Illustration of binary vector 24217.

FIG. 2 shows photographs of rust bioassay experiments conducted on leaves collected from primary soybean events generated from binary vector 24217.

FIG. 3 is a graph showing relative expression (y-axis) of soybean rust β-tubulin gene in construct 24217 primary soybean events at 14 days post inoculation.

FIG. 4 is a graph showing relative expression (y-axis) of *G. canescens* TIR-A and TIR-B genes in transgenic soybean events conferring resistance to soybean rust.

FIG. 5 is graph summarizing qRT-PCR analysis of GVG00885565 T1-generation plants that are homozygous or heterozygous for TIR-A and TIR-B genes.

FIG. 6 shows photographs of T1-generation null and homozygous GVG00885565 plants 14 days post-inoculation with three different soybean rust populations.

FIG. 7 is a graph summarizing the relative expression (y-axis) of soybean rust β-tubulin gene at 8, 14 and 21 days post-inoculation in the null and TIR-A, TIR-B homozygous plants.

FIG. 8A is an illustration of a binary vector map of TIR-A (24205) used in co-transformation experiments.

FIG. 8B is an illustration of a binary vector map of TIR-B (24192) used in co-transformation experiments.

FIG. 9. Foliar symptoms correlating to qRT assay.

FIG. 10 is an illustration of binary vector 23891.

FIG. 11 is a depiction of *Glycine canescens* PI440935 SNPs associated with ASR Resistance (i.e. each dot equals 1 SNP that associates with ASR resistance).

FIG. 12 is a depiction of *Glycine canescens* PI440935 SNPs associated with ASR Resistance with chromosome number (i.e. each dot equals 1 SNP that associates with ASR resistance).

FIG. 13 shows SNP charts related to mapping intervals for Scaffold 000056F.

FIG. 14 depicts *Glycine clandestina* PI339656 SNPs associated with ASR Resistance (i.e. each dot equals 1 SNP that associates with ASR resistance; scaffold 14851 (Chr14) & scaffold 9588 (CHR9).

FIG. 15 shows SNP charts related to mapping intervals for Scaffold 14851.

BRIEF DESCRIPTION OF THE SEQUENCE LISTING

SEQ ID NO: 1 is a chromosomal interval derived from *Glycine canescens* line accession PI440935 referred to herein as “Scaffold 000056F. Scaffold 000056F has been mapped to *G. canescens* chromosome 14. SEQ ID NO. 2 is a chromosomal interval derived from *Glycine canescens* line accessions PI595799 referred to herein as “Scaffold 000090F”. Scaffold 000090F has been mapped to *G. canescens* chromosome 14. SEQ ID NO: 3 is a chromosomal interval derived from *Glycine canescens* line accession PI 483193 referred to herein as “Scaffold 92F”. Scaffold 132F has been mapped to *G. canescens* chromosome 14. SEQ ID NO: 4 is a chromosomal intervals derived from *Glycine clandestina* line accession PI339656 referred to herein as “Scaffold 14851”. Scaffold 14851 has been mapped to *G. clandestina* chromosome 14 at an approximate interval of 3.18 to 3.50 MB on Scaffold 14851. These chromosomal intervals or portions thereof may be introduced (i.e. introgressed through use of embryo rescue and/or marker assisted breeding (MAB)) into *Glycine max* lines to create *Glycine max* lines resistant to disease (e.g. Asian Soybean Rust (ASR)). SEQ ID NO: 5 is a chromosomal intervals derived from *Glycine tomentella* line accession PI509501 referred to herein as “Scaffold 4269. SEQ ID NO: 6 is a chromosomal intervals derived from *Glycine tomentella* line accession PI509501 referred to herein as "Scaffold 1509". Scaffolds 4269 and 1509 have been mapped to *G. tomentella* chromosome 14.

Further research into the intervals led to the discovery of causative genes and associated native promoters and terminator sequences were identified from the above interval(s) located on or corresponding to *G. canescens* and *G. clandestina* Chromosome 14.

SEQ ID NO: 7 is genomic DNA for a soy rust resistance gene (also referred to herein as the "TIR-A gene") from PI595799 encoding a protein containing Toll/Interleukin-1 receptor (a "TIR" R-gene motif) domain synthetic to Glyma.05G165800 (Soy_william82_v2). SEQ ID NO: 8 is a cDNA sequence for the TIR-A gene. SEQ ID NO: 9 comprises an exemplary promoter for either of SEQ ID NOs: 7 or 8. SEQ ID NO: 9 comprises and an exemplary terminator sequence for either of SEQ ID NOs: 7 or 8. SEQ ID NOs: 7 and 8 encodes the protein of SEQ ID NO: 11.

SEQ ID NO: 12 is genomic DNA for another soy rust resistance gene (also referred to herein as the TIR-B gene") having a TIR R-gene motif. SEQ ID NO: 13 is a cDNA sequence for the TIR-B gene. SEQ ID NO: 14 comprises an exemplary promoter for either of SEQ ID NOs: 12 or 13. SEQ ID NO: 15 comprises and an exemplary terminator sequence for either of SEQ ID NOs: 12 or 13. SEQ ID NOs: 12 or 13 encode the protein of SEQ ID NO: 16.

ASR resistance can be introduced into *G. max* plants using SEQ ID NOs: 7, 8, 11, 12 or any combination there. It is further contemplated that ASR resistance can be introduced into elite Soybean plants either via transgenic expression of genes encoding a protein having a TIR R-gene motif or a gene having between 70-100% homology to any of SEQ ID NOs: 7, 8, 11, 12.

SEQ ID NO: 17 is a DNA sequence for Vector 24217_*G. canescens* PI595799-cGcaRG3b-02 which is a N-terminal truncated version of TIR-B component.

SEQ ID NO: 18 is a DNA sequence for Vector 23819_*G. clandestina* PI339656-Genomic TIR-A and TIR-B.

SEQ ID NO: 19 is a DNA sequence for promoter AtEF1aA1, which is derived from the *Arabidopsis thaliana* Elongation Factor EF-1 alpha A1 gene.

SEQ ID NO: 20 is a DNA sequence for prUBQ3, which is a modified version of *Arabidopsis* Ubiquitin 3 promoter.

SEQ ID NO: 21 is a DNA sequence for prGmUbi1, which is a Ubiquitin 1 promoter from soybean.

SEQ ID NO: 22 is a DNA sequence from prLuFIS1, which is a 660 bp fragment of the first promoter from flax (*Linum usitatissimum*).

SEQ ID NO: 23 is the DNA sequence for a primer for TIR-B.

SEQ ID NO: 24 is the DNA sequence for a primer for TIR-B.

SEQ ID NO: 25 is the DNA sequence for a probe for TIR-B.

SEQ ID NO: 26 is the DNA sequence for a primer for TIR-A.

SEQ ID NO: 27 is the DNA sequence for a primer for TIR-A.

SEQ ID NO: 28 is the DNA sequence for a probe for TIR-A.

SEQ ID NO: 29 is the DNA sequence for a primer for TIR-A.

SEQ ID NO: 30 is the DNA sequence for a primer for TIR-A.

SEQ ID NO: 31 is the DNA sequence for a probe for TIR-A.

SEQ ID NO: 32 is the DNA sequence for Vector 24205.

SED ID NO: 33 is the DNA sequence for Vector 24192.

DETAILED DESCRIPTION OF THE INVENTION

The presently disclosed subject matter relates to compositions and methods for introducing novel resistance genes (herein, "R-Genes") into commercial soybean plants to control soybean pathogens. The methods involve transforming organisms with nucleotide sequences encoding the R-genes of the invention. The nucleotide sequences of the invention are useful for generating plants that show increased resistance to soybean pathogens, particularly Asian Soybean Rust (herein, "ASR"). Thus, transformed plants, plant cells, plant tissues and seeds are provided. Compositions include nucleic acids and proteins relating to soybean pathogen resistant plants as well as transformed plants, plant tissues and seeds. Nucleotide sequences of the R-genes and the amino acid sequences of the proteins encoded thereby are disclosed. The sequences find use in the construction of expression vectors for subsequent transformation into plants of interest, as probes for the isolation of other R-genes, and the like.

It is possible to produce soybean pathogen resistant plants by inserting into the plant genome a DNA molecule that provides for resistance (Cook et al, 2012 for SCN resistance; Kawashima et al., 2016 for soy rust resistance from pigeon pea).

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

All references listed below, as well as all references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

Nucleotide sequences provided herein are presented in the 5' to 3' direction, from left to right and are presented using the standard code for representing nucleotide bases as set forth in 37 CFR §§ 1.821-1.825 and the World Intellectual Property Organization (WIPO) Standard ST.25, for example: adenine (A), cytosine (C), thymine (T), and guanine (G).

Amino acids are likewise indicated using the WIPO Standard ST.25, for example: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Definitions

Unless defined otherwise, all technical and scientific terms used herein have the same meaning as commonly understood to one of ordinary skill in the art to which the presently disclosed subject matter belongs.

Although the following terms are believed to be well understood by one of ordinary skill in the art, the following definitions are set forth to facilitate understanding of the presently disclosed subject matter.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount. As used herein, phrases such as "between about X and Y" mean "between about X and about Y" and phrases such as "from about X to Y" mean "from about X to about Y."

As used herein, phrases such as "between about X and Y", "between about X and about Y", "from X to Y" and "from about X to about Y" (and similar phrases) should be interpreted to include X and Y, unless the context indicates otherwise.

A "coding sequence" is a nucleic acid sequence that is transcribed into RNA such as mRNA, rRNA, tRNA, snRNA, sense RNA or antisense RNA. In embodiments, the RNA is then translated to produce a protein.

As used herein, a "codon optimized" nucleotide sequence means a nucleotide sequence of a recombinant, transgenic, or synthetic polynucleotide wherein the codons are chosen to reflect the particular codon bias that a host cell or organism may have. This is typically done in such a way so as to preserve the amino acid sequence of the polypeptide encoded by the codon optimized nucleotide sequence. In certain embodiments, a nucleotide sequence is codon optimized for the cell (e.g., an animal, plant, fungal or bacterial cell) in which the construct is to be expressed. For example, a construct to be expressed in a plant cell can have all or parts of its sequence codon optimized for expression in a plant. See, for example, U.S. Pat. No. 6,121,014. In embodiments, the polynucleotides of the invention are codon-optimized for expression in a plant cell (e.g., a dicot cell or a monocot cell) or bacterial cell.

The term "comprise", "comprises" or "comprising," when used in this specification, indicates the presence of the stated features, integers, steps, operations, elements, or components, but does not preclude the presence or addition of one or more other features, integers, steps, operations, elements, components, and/or groups thereof.

As used herein, the transitional phrase "consisting essentially of" (and grammatical variants) means that the scope of a claim is to be interpreted to encompass the specified materials or steps recited in the claim "and those that do not materially alter the basic and novel characteristic(s)" of the claimed invention. Thus, the term "consisting essentially of" when used in a claim of this invention is not intended to be interpreted to be equivalent to "comprising."

"Expression cassette" as used herein means a nucleic acid molecule capable of directing expression of at least one polynucleotide of interest, such as a R-gene polynucleotide that encodes protein of the invention, in an appropriate host cell, comprising a promoter operably linked to the polynucleotide of interest which is operably linked to a termination signal. An "expression cassette" also typically comprises additional polynucleotides to facilitate proper translation of the polynucleotide of interest. The expression cassette may also comprise other polynucleotides not related to the expression of a polynucleotide of interest but which are present due to convenient restriction sites for removal of the cassette from an expression vector. In embodiments, at least one of the components in the expression cassette may be heterologous (i.e, foreign) with respect to at least one of the other components (e.g., a heterologous promoter operatively associated with a polynucleotide of interest). The expression cassette may also be one that is naturally occurring but has been obtained in a recombinant form useful for heterologous expression. Typically, however, the expression cassette is heterologous with respect to the host, i.e, the expression cassette (or even the polynucleotide of interest) does not occur naturally in the host cell and has been introduced into the host cell or an ancestor cell thereof by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development (as described in more detail herein). An expression cassette, or fragment thereof, can also be referred to as "inserted polynucleotide" or "insertion polynucleotide" when transformed into a plant.

A "gene" is defined herein as a hereditary unit comprising one or more polynucleotides that occupies a specific location on a chromosome or plasmid and that contains the genetic instruction for a particular characteristic or trait in an organism.

The term "introduced" as used herein, in connection to a plant, means accomplished by any manner including but not limited to; introgression, transgenic, Clustered Regularly Interspaced Short Palindromic Repeats modification (CRISPR), Transcription activator-like effector nucleases (TALENs) (Feng et al. 2013, Joung & Sander 2013), meganucleases, or zinc finger nucleases (ZFNs).

As used herein, the term "wild glycine" refers to a perennial *Glycine* plant, for example any one of *G. canescens, G. argyrea, G. clandestina, G. latrobeana, G. albicans, G. aphyonota, G. arenaria, G. curvata, G. cyrtoloba, G. dolichocarpa, G. falcate, G. gracei, G. hirticaulis, G. lactovirens, G. latifolia, G. microphylla, G. montis-clouglas, G. peratosa, G. pescadrensis, G. pindanica, G. pulleng G. rubiginosa, G. stenophita, G. syndetika*, or *G. tomentella.*

As used herein, the term "allele" refers to one of two or more different nucleotides or nucleotide sequences that occur at a specific locus.

A marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with enhanced pathogen resistance" refers to a marker whose presence or absence can be used to predict whether and/or to what extent a plant will display a pathogen resistant phenotype.

As used herein, the terms "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, In Techniques et Utilisations Des Marqueurs Moleculaires Les Colloques, Vol. 72, pp. 45-56 (1995); and Openshaw et al., *Marker-assisted Selection in Backcross Breeding*, in Proceedings of the Symposium "Analysis of Molecular Marker Data," pp. 41-53 (1994). The initial cross gives rise to the F1 generation. The term "BC1" refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval defined by and including," used in reference to particular loci and/or alleles, refers to a chromosomal interval delimited by and encompassing the stated loci/alleles.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "desired allele", "favorable allele" and "allele of interest" are used interchangeably to refer to an allele associated with a desired trait (e.g. ASR resistance).

As used herein, the terms "enhanced pathogen resistance" or "enhanced disease resistance" refers to an improvement, enhancement, or increase in a plant's ability to endure and/or thrive despite being infected with a disease (e.g. Asian soybean rust) as compared to one or more control plants (e.g., one or both of the parents, or a plant lacking a marker associated with enhanced pathogen resistance to respective pathogen/disease). Enhanced disease resistance includes any mechanism (other than whole-plant immunity or resistance) that reduces the expression of symptoms indicative of infection for a respective disease such as Asian soybean rust, soybean cyst nematode, *Phytophthora*, etc.

An "elite line" or "elite strain" is an agronomically superior line that has resulted from many cycles of breeding and selection for superior agronomic performance. Numerous elite lines are available and known to those of skill in the art of soybean breeding. An "elite population" is an assortment of elite individuals or lines that can be used to represent the state of the art in terms of agronomically superior genotypes of a given crop species, such as soybean. Similarly, an "elite germplasm" or elite strain of germplasm is an agronomically superior germplasm, typically derived from and/or capable of giving rise to a plant with superior agronomic performance, such as an existing or newly developed elite line of soybean.

An "elite" plant is any plant from an elite line, such that an elite plant is a representative plant from an elite variety. Non-limiting examples of elite soybean varieties that are commercially available to farmers or soybean breeders include: AG00802, A0868, AG0902, A1923, AG2403, A2824, A3704, A4324, A5404, AG5903, AG6202 AG0934; AG1435; AG2031; AG2035; AG2433; AG2733; AG2933; AG3334; AG3832; AG4135; AG4632; AG4934; AG5831; AG6534; and AG7231 (Asgrow Seeds, Des Moines, Iowa, USA); BPR0144RR, BPR 4077NRR and BPR 4390NRR (Bio Plant Research, Camp Point, Ill., USA); DKB17-51 and DKB37-51 (DeKalb Genetics, DeKalb, Ill., USA); DP 4546 RR, and DP 7870 RR (Delta & Pine Land Company, Lubbock, Tex., USA); JG 03R501, JG 32R606C ADD and JG 55R503C (JGL Inc., Greencastle, Ind., USA); NKS 13-K2 (NK Division of Syngenta Seeds, Golden Valley, Minnesota, USA); 90M01, 91M30, 92M33, 93M11, 94M30, 95M30, 97652, P008T22R2; P16T17R2; P22T69R; P25T51R; P34T07R2; P35T58R; P39T67R; P47T36R; P46T21R; and P56T03R2 (Pioneer Hi-Bred International, Johnston, Iowa, USA); SG4771NRR and SG5161NRR/STS (Soygenetics, LLC, Lafayette, Ind., USA); S00-K5, S11-L2, 528-Y2, S43-61, S53-A1, 576-L9, S78-G6, 50009-M2; S007-Y4; 504-D3; 514-A6; S20-T6; 521-M7; S26-P3; S28-N6; S30-V6; S35-C3; 536-Y6; S39-C4; S47-K5; S48-D9; S52-Y2; 558-Z4; S67-R6; S73-S8; and S78-G6 (Syngenta Seeds, Henderson, Ky., USA); Richer (Northstar Seed Ltd. Alberta, CA); 14RD62 (Stine Seed Co. la., USA); or Armor 4744 (Armor Seed, LLC, Ar., USA).

The terms "agronomically elite" as used herein, means a genotype that has a culmination of many distinguishable traits such as emergence, vigor, vegetative vigor, disease resistance, seed set, standability, yield and threshability which allows a producer to harvest a product of commercial significance.

As used herein, the term "commercially significant yield" or "agronomically acceptable yield" refers to a grain yield of at least 100% of a commercial check variety such as AG2703 or DKB23-51.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism.

The terms "nucleic acid," "nucleic acid molecule," "nucleotide sequence," "oligonucleotide", "polynucleic acids" and "polynucleotide" are used interchangeably herein, unless the context indicates otherwise, and refer to a heteropolymer of nucleotides. These terms include without limitation DNA and RNA molecules, including cDNA, genomic DNA, synthetic (e.g., chemically synthesized) DNA and RNA, plasmid DNA, mRNA, anti-sense RNA, and RNA/DNA hybrids, any of which can be linear or branched, single stranded or double stranded, or a combination thereof. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. In embodiments, the "nucleic acid," "nucleic acid molecule,", "nucleotide sequence,", "oligonucleotide" or "polynucleotide" refer to DNA.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence, means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to or "operatively associated" with the nucleotide sequence.

As used herein, the terms "disease tolerance" and "disease resistant" refer to a plant's ability to endure and/or thrive despite being infected with a respective disease. When used in reference to germplasm, the terms refer to the ability of a plant that arises from that germplasm to endure and/or thrive despite being infected with a respective disease. In some embodiments, infected Disease resistant soybean plants may yield as well (or nearly as well) as uninfected soybean plants. In general, a plant or germplasm is labeled as "Disease resistant" if it displays "enhanced pathogen resistance."

As used herein, the term "endogenous" refers to materials originating from within an organism or cell. "Exogenous" refers to materials originating from outside of an organism or cell. This typically applies to nucleic acid molecules used in producing transformed or transgenic host cells and plants.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, a "genetic map" is a description of genetic linkage relationships among loci on one or more chromosomes within a given species, generally depicted in a diagrammatic or tabular form. For each genetic map, distances between loci are measured by the recombination frequencies between them. Recombinations between loci can be detected using a variety of markers. A genetic map is a product of the mapping population, types of markers used, and the polymorphic potential of each marker between different populations. The order and genetic distances between loci can differ from one genetic map to another.

As used herein, the term "genome" as it applies to plant cells encompasses not only chromosomal DNA found within the nucleus, but organelle DNA found within subcellular components of the cell. The term "gene" refers to polynucleic acids that comprise chromosomal DNA, plasmid DNA, cDNA, an artificial DNA polynucleotide, or other DNA that is transcribed into an RNA molecule, wherein the RNA may encode a peptide, polypeptide, or protein, and the genetic elements flanking the coding sequence that are involved in the regulation of expression of the mRNA or polypeptide of the present invention. A "fragment" of a gene is a portion of a full-length polynucleic acid molecule that is of at least a minimum length capable of transcription into a RNA, translation into a peptide, or useful as a probe or primer in a DNA detection method.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm may refer to seeds, cells (including protoplasts and calli) or tissues from which new plants may be grown, as well as plant parts that can be cultured into a whole plant (e.g., stems, buds, roots, leaves, etc.).

As used herein, a "Heterologous DNA" sequence refers to a polynucleotide sequence that originates from a foreign source or species or, if from the same source, is modified from its original form.

As used herein, a "Homologous DNA" refers to DNA from the same source as that of the recipient cell.

As used herein, the term "hybrid" refers to a seed and/or plant produced when at least two genetically dissimilar parents are crossed.

As used herein, the term "inbred" refers to a substantially homozygous plant or variety. The term may refer to a plant or variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be repeatedly backcrossed to a line having a desired genetic background and selected for the desired allele, with the result being that the desired allele becomes fixed in the desired genetic background. For example, a marker associated with enhanced ASR tolerance may be introgressed from a donor into a recurrent parent that is not disease resistant. The resulting offspring could then be repeatedly backcrossed and selected until the progeny possess the ASR tolerance allele(s) in the recurrent parent background.

As used herein, an "isolated" nucleic acid molecule is substantially separated away from other nucleic acid sequences with which the nucleic acid is normally associated, such as, from the chromosomal or extrachromosomal DNA of a cell in which the nucleic acid naturally occurs. A nucleic acid molecule is an isolated nucleic acid molecule when it comprises a transgene or part of a transgene present in the genome of another organism. The term also embraces nucleic acids that are biochemically purified so as to substantially remove contaminating nucleic acids and other cellular components. The term "transgene" refers to any polynucleic acid molecule normative to a cell or organism transformed into the cell or organism. "Transgene" also encompasses the component parts of a native plant gene modified by insertion of a normative polynucleic acid molecule by directed recombination or site specific mutation.

A polypeptide is "isolated" if it has been separated from the cellular components (nucleic acids, lipids, carbohydrates, and other polypeptides) that naturally accompany it or that is chemically synthesized or recombinant. A polypeptide molecule is an isolated polypeptide molecule when it is expressed from a transgene in another organism. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods. Proteins can be purified by any of the means known in the art, for example as described in Guide to Protein Purification, ed. Deutscher, Meth. Enzymol. 185, Academic Press, San Diego, 1990; and Scopes, Protein Purification: Principles and Practice, Springer Verlag, New York, 1982.

Using well-known methods, the skilled artisan can readily produce nucleotide and amino acid sequence variants of genes and proteins that provide a modified gene product. Chemical synthesis of nucleic acids can be performed, for example, on automated oligonucleotide synthesizers. Such variants preferably do not change the reading frame of the protein-coding region of the nucleic acid. The present invention also encompasses fragments of a protein that lacks at least one residue of a full-length protein, but that substantially maintains activity of the protein.

A "locus" is a position on a chromosome where a gene or marker or allele is located. In some embodiments, a locus may encompass one or more nucleotides.

A "non-naturally occurring variety of soybean" is any variety of soybean that does not naturally exist in nature. A "non-naturally occurring variety of soybean" may be produced by any method known in the art, including, but not limited to, transforming a soybean plant or germplasm, transfecting a soybean plant or germplasm and crossing a naturally occurring variety of soybean with a non-naturally occurring variety of soybean. In some embodiments, a "non-naturally occurring variety of soybean" may comprise one of more heterologous nucleotide sequences. In some embodiments, a "non-naturally occurring variety of soybean" may comprise one or more non-naturally occurring copies of a naturally occurring nucleotide sequence (i.e, extraneous copies of a gene that naturally occurs in soybean). In some embodiments, a "non-naturally occurring variety of soybean" may comprise a non-natural combination of two or more naturally occurring nucleotide sequences (Le, two or more naturally occurring genes that do not naturally occur in the same soybean, for instance genes not found in *Glycine max* lines).

As used herein, the terms "phenotype," "phenotypic trait" or "trait" refer to one or more traits and/or manifestations of an organism. The phenotype can be a manifestation that is observable to the naked eye, or by any other means of evaluation known in the art, e.g., microscopy, biochemical analysis, or an electromechanical assay. In some cases, a phenotype or trait is directly controlled by a single gene or genetic locus, i.e., a "single gene trait." In other cases, a phenotype or trait is the result of several genes. It is noted that, as used herein, the term "disease resistant phenotype" takes into account environmental conditions that might affect the respective disease such that the effect is real and reproducible.

As used herein, the term "plant" may refer to a whole plant, any part thereof, or a cell or tissue culture derived from a plant. Thus, the term "plant" can refer to any of: whole plants, plant components or organs (e.g., roots, stems, leaves, buds, flowers, pods, etc.), plant tissues, seeds and/or plant cells. A plant cell is a cell of a plant, taken from a plant, or derived through culture from a cell taken from a plant. Thus, the term "soybean plant" may refer to a whole soybean plant, one or more parts of a soybean plant (e.g., roots, root tips, stems, leaves, buds, flowers, pods, seeds, cotyledons, etc.), soybean plant cells, soybean plant protoplasts and/or soybean plant calli.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant. In embodiments, the plant cell is non-propagating and/or cannot regenerate a whole plant.

A "plant cell culture" means a culture of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

As used herein, the term "plant part" includes but is not limited to embryos, pollen, ovules, seeds, leaves, flowers, branches, fruit, stalks, roots, root tips, anthers, and/or plant cells including plant cells that are intact in plants and/or parts of plants, plant protoplasts, plant tissues, plant cell tissue cultures, plant calli, plant clumps, and the like.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural or functional units. The use of this term in conjunction with, or in the absence of, any specific type of plant tissue as listed above or otherwise embraced by this definition is not intended to be exclusive of any other type of plant tissue.

"Polyadenylation signal" or "polyA signal" refers to a nucleic acid sequence located 3' to a coding region that causes the addition of adenylate nucleotides to the 3' end of the mRNA transcribed from the coding region.

"Polymerase chain reaction (PCR)" refers to a DNA amplification method that uses an enzymatic technique to create multiple copies of one sequence of nucleic acid (amplicon). Copies of a DNA molecule are prepared by shuttling a DNA polymerase between two amplimers. The basis of this amplification method is multiple cycles of temperature changes to denature, then re-anneal amplimers (DNA primer molecules), followed by extension to synthesize new DNA strands in the region located between the flanking amplimers. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of the primer can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing. Primers can be prepared by any suitable method known in the art. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066. Primers can be labeled, if desired, by incorporating detectable moieties by for instance spectroscopic, fluorescence, photochemical, biochemical, immunochemical, or chemical moieties. Primers diagnostic (i.e. able to identify or select based on presence of ASR resistant alleles) for ASR resistance can be created to any favorable SNP as described in any one of Tables 1-5. The PCR method is well described in handbooks and known to the skilled person. After amplification by PCR, target polynucleotides can be detected by hybridization with a probe polynucleotide, which forms a stable hybrid with the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). Molecular Cloning: A Laboratory Manual, Third Edition, Cold Spring Harbor Laboratory Press, Cold Spring Harbor, New York, United States of America. Generally, lower salt concentration and higher temperature hybridization and/or washes increase the stringency of hybridization conditions.

As used herein, the terms "progeny" and "progeny plant" refer to a plant generated from a vegetative or sexual reproduction from one or more parent plants. A progeny plant may be obtained by cloning or selfing a single parent plant, or by crossing two parental plants.

The term "promoter" or "promoter region" refers to a polynucleic acid molecule that functions as a regulatory element, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant DNA construct, as demonstrated by its ability to produce mRNA.

A "recombinant" nucleic acid is made by a combination of two otherwise separated segments of nucleic acid sequence, for example, by chemical synthesis or by the manipulation of isolated segments of polynucleic acids by genetic engineering techniques. The term "recombinant DNA construct" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule that one or more DNA sequences have been linked in a functionally operative manner. Such recombinant DNA constructs are capable of introducing a 5' regulatory sequence or promoter region and a DNA sequence for a selected gene product into a cell in such a manner that the DNA sequence is transcribed into a functional mRNA that is translated and therefore expressed.

Recombinant DNA constructs may be constructed to be capable of expressing antisense RNAs, or stabilized double stranded antisense RNAs.

The phrase "substantially identical," in the context of two nucleic acids or two amino acid sequences, refers to two or more sequences or subsequences that have at least about 50% nucleotide or amino acid residue identity when compared and aligned for maximum correspondence as measured using a sequence comparison algorithm or by visual inspection. In certain embodiments, substantially identical sequences have at least about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more nucleotide or amino acid residue identity. In certain embodiments, substantial identity exists over a region of the sequences that is at least about 50 amino acid residues, 100 amino acid residues, 150 amino acid residues, 200 amino acid residues, 250 amino acid residues, 300 amino acid residues, 350 amino acid residues, 400 amino acid residues, 450 amino acid residues, 500 amino acid residues, 525 amino acid residues, 526, amino acid residues 527 amino acid residues, 528 amino acid residues, 529 amino acid residues, 530 amino acid residues, 531 amino acid residues, 532 amino acid residues, 533 amino acid residues, 534 amino acid residues, 535 amino acid residues, 536 amino acid residues or more with respect to the protein sequence or the nucleotide sequence encoding the same. In further embodiments, the sequences are substantially identical when they are identical over the entire length of the coding regions.

"Identity" or "percent identity" refers to the degree of identity between two nucleic acid or amino acid sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., J. Mol. Biol. 215: 403-410 (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity. In addition to identity positions, consensus positions are also commonly scored. Consensus amino acids are those known to have similar amino acid properties such as charge, size, polarity, and aromaticity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a nucleic acid will selectively hybridize to a target sequence to a detectably greater degree than other sequences (e.g., at least 2-fold over a non-target sequence), and optionally may substantially exclude binding to non-target sequences. Stringent conditions are sequence-dependent and will vary under different circumstances. By controlling the stringency of the hybridization and/or washing conditions, target sequences can be identified that can be up to 100% complementary to the reference nucleotide sequence. Alternatively, conditions of moderate or even low stringency can be used to allow some mismatching in sequences so that lower degrees of sequence similarity are detected. For example, those skilled in the art will appreciate that to function as a primer or probe, a nucleic acid sequence only needs to be sufficiently complementary to the target sequence to substantially bind thereto so as to form a stable double-stranded structure under the conditions employed. Thus, primers or probes can be used under conditions of high, moderate or even low stringency. Likewise, conditions of low or moderate stringency can be advantageous to detect homolog, ortholog and/or paralog sequences having lower degrees of sequence identity than would be identified under highly stringent conditions.

The terms "complementary" or "complementarity" (and similar terms), as used herein, refer to the natural binding of polynucleotides under permissive salt and temperature conditions by base-pairing. For example, the sequence "A-G-T" binds to the complementary sequence "T-C-A." Complementarity between two single-stranded molecules may be partial, in which only some of the nucleotides bind, or it may be complete when total complementarity exists between the single stranded molecules. The degree of complementarity between nucleic acid strands has significant effects on the efficiency and strength of hybridization between the molecules. As used herein, the term "substantially complementary" (and similar terms) means that two nucleic acid sequences are at least about 50%, 60%, 70%, 75%, 80%, 85%, 90%, 95%, 96%, 97%, 98%, 99% or more complementary. Alternatively, the term "substantially complementary" (and similar terms) can mean that two nucleic acid sequences can hybridize together under high stringency conditions (as described herein).

As used herein, "specifically" or "selectively" hybridizing (and similar terms) refers to the binding, duplexing, or hybridizing of a molecule to a particular nucleic acid target sequence under stringent conditions when that sequence is present in a complex mixture (e.g., total cellular DNA or RNA) to the substantial exclusion of non-target nucleic acids, or even with no detectable binding, duplexing or hybridizing to non-target sequences. Specifically or selectively hybridizing sequences typically are at least about 40% complementary and are optionally substantially complementary or even completely complementary (i.e., 100% identical).

For DNA-DNA hybrids, the $T_m$ can be approximated from the equation of Meinkoth and Wahl, Anal. Biochem., 138: 267-84 (1984): $T_m$=81.5° C.+16.6 (log M)+0.41 (% GC)-0.61 (% formamide)-500/L; where M is the molarity of monovalent cations, % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired degree of identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, highly stringent conditions can utilize a hybridization and/or wash at the thermal melting point ($T_m$) or 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). If the desired degree of mismatching results in a $T_m$ of less than 45° C. (aqueous solution) or 32° C. (formamide solution), optionally the SSC concentration can be increased so that a higher temperature can be used. An extensive guide to the hybridization of nucleic acids is found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier, New York (1993); Current Protocols in Molecular Biology, chapter 2, Ausubel, et al., eds, Greene Publishing and Wiley-Interscience, New York (1995); and Green & Sambrook, In: Molecular Cloning, A Laboratory Manual, 4th Edition, Cold Spring Harbor Press, Cold Spring Harbor, N.Y. (2012).

Typically, stringent conditions are those in which the salt concentration is less than about 1.5 M Na ion, typically about 0.01 to 1.0 M Na ion concentration (or other salts) at about pH 7.0 to pH 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide or Denhardt's (5 g Ficoll, 5 g polyvinylpyrrolidone, 5 g bovine serum albumin in 500 ml of water). Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. A further non-limiting example of high stringency conditions include hybridization in 4×SSC, 5×Denhardt's, 0.1 mg/ml boiled salmon sperm DNA, and 25 mM Na phosphate at 65° C. and a wash in 0.1×SSC, 0.1% SDS at 65° C. Another illustration of high stringency hybridization conditions includes hybridization in 7% SDS, 0.5 M $NaPO_4$, 1 mM EDTA at 50° C. with washing in 2×SSC, 0.1% SDS at 50° C., alternatively with washing in 1×SSC, 0.1% SDS at 50° C., alternatively with washing in 0.5×SSC, 0.1% SDS at 50° C., or alternatively with washing in 0.1×SSC, 0.1% SDS at 50° C., or even with washing in 0.1×SSC, 0.1% SDS at 65° C. Those skilled in the art will appreciate that specificity is typically a function of post-hybridization washes, the relevant factors being the ionic strength and temperature of the final wash solution.

Nucleic acids that do not hybridize to each other under stringent conditions are still substantially identical if the proteins that they encode are substantially identical (e.g., due to the degeneracy of the genetic code).

A further indication that two nucleic acids or proteins are substantially identical is that the protein encoded by the first nucleic acid is immunologically cross reactive with the protein encoded by the second nucleic acid. Thus, a protein is typically substantially identical to a second protein, for example, where the two proteins differ only by conservative substitutions.

The term "vector" refers to a composition for transferring, delivering or introducing a nucleic acid (or nucleic acids) into a cell. A vector comprises a nucleic acid molecule comprising the nucleotide sequence(s) to be transferred, delivered or introduced.

Expression of an R-Gene Coding Sequence in Plants

DNA constructs are made that contain various genetic elements necessary for the expression of the R-Gene coding sequence in plants, thereby imparting pathogen resistance to the plants in which they are expressed. "DNA construct" refers to the heterologous genetic elements operably linked to each other making up a recombinant DNA molecule and may comprise elements that provide expression of a DNA polynucleotide molecule in a host cell and elements that provide maintenance of the construct in the host cell. A plant expression cassette comprises the operable linkage of genetic elements that when transferred into a plant cell provides expression of a desirable gene product. "Plant expression cassette" refers to chimeric DNA segments comprising the regulatory elements that are operably linked to provide the expression of a transgene product in plants. Promoters, leaders, introns, transit peptide encoding polynucleic acids, 3' transcriptional termination regions are all genetic elements that may be operably linked by those skilled in the art of plant molecular biology to provide a desirable level of expression or functionality to an R-gene of the present invention. A DNA construct can contain one or more plant expression cassettes expressing the DNA molecules of the present invention or other DNA molecules useful in the genetic engineering of crop plants.

A variety of promoters specifically active in vegetative tissues, such as leaves, stems, roots and tubers, can be used to express the R-gene polynucleic acid molecules of the present invention.

The translation leader sequence means a DNA molecule located between the promoter of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders, plant virus coat protein leaders, plant rubisco gene leaders among others (Turner and Foster, Molecular Biotechnology 3:225, 1995).

The "3' non-translated sequences" means DNA sequences located downstream of a structural polynucleotide sequence and include sequences encoding polyadenylation and other regulatory signals capable of affecting mRNA processing or gene expression. The polyadenylation signal functions in plants to cause the addition of multiple adenylate nucleotides to the 3' end of the mRNA precursor. The polyadenylation sequence can be derived from the natural gene, from a variety of plant genes, or from T-DNA. An example of the polyadenylation sequence is the nopaline synthase 3' sequence (nos 3'; Fraley et al., Proc. Natl. Acad. Sci. USA 80: 4803-4807, 1983). The use of different 3' non-translated sequences is exemplified by Ingelbrecht et al., Plant Cell 1:671-680, 1989.

The laboratory procedures in recombinant DNA technology used herein are those well-known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al. (1989).

The DNA construct of the present invention may be introduced into the genome of a desired plant host by a variety of conventional transformation techniques that are well known to those skilled in the art. "Transformation" refers to a process of introducing an exogenous polynucleic acid molecule (for example, a DNA construct, a recombinant polynucleic acid molecule) into a cell or protoplast and that exogenous polynucleic acid molecule is incorporated into a host cell genome or an organelle genome (for example, chloroplast or mitochondria) or is capable of autonomous replication. "Transformed" or "transgenic" refers to a cell, tissue, organ, or organism into which a foreign polynucleic acid, such as a DNA vector or recombinant polynucleic acid molecule. A "transgenic" or "transformed" cell or organism also includes progeny of the cell or organism and progeny produced from a breeding program employing such a "transgenic" plant as a parent in a cross and exhibiting an altered phenotype resulting from the presence of the foreign polynucleic acid molecule.

Methods of transformation of plant cells or tissues include, but are not limited to *Agrobacterium* mediated transformation method and the Biolistics or particle-gun mediated transformation method. Suitable plant transformation vectors for the purpose of *Agrobacterium* mediated transformation include-those elements derived from a tumor inducing (Ti) plasmid of *Agrobacterium tumefaciens*, for example, right border (RB) regions and left border (LB) regions, and others disclosed by Herrera-Estrella et al., Nature 303:209 (1983); Bevan, Nucleic Acids Res. 12:8711-8721 (1984); Klee et al., Bio-Technology 3(7):637-642 (1985). In addition to plant transformation vectors derived from the Ti or root-inducing (Ri) plasmids of *Agrobacterium*, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

DNA constructs can be prepared that incorporate the R-gene coding sequences of the present invention for use in directing the expression of the sequences directly from the host plant cell plastid. Examples of such constructs suitable for this purpose and methods that are known in the art and are generally described, for example, in Svab et al., Proc. Natl. Acad. Sci. USA 87:8526-8530, (1990) and Svab et al., Proc. Natl. Acad. Sci. USA 90:913-917 (1993) and in U.S. Pat. No. 5,693,507.

When adequate numbers of cells containing the exogenous polynucleic acid molecule encoding polypeptides from the present invention are obtained, the cells can be cultured, then regenerated into whole plants. "Regeneration" refers to the process of growing a plant from a plant cell (for example, plant protoplast or explant). Such regeneration techniques rely on manipulation of certain phytohormones in a tissue culture growth medium, typically relying on a biocide and/or herbicide marker that has been introduced together with the desired nucleotide sequences. Choice of methodology for the regeneration step is not critical See, for example, Ammirato et al., Handbook of Plant Cell Culture—Crop Species. Macmillan Publ. Co. (1984); Shimamoto et al., Nature 338:274-276 (1989); Fromm, UCLA Symposium on Molecular Strategies for Crop Improvement, Apr. 16-22, 1990. Keystone, Colo. (1990); Vasil et al., Bio/Technology 8:429-434 (1990); Vasil et al., Bio/Technology 10:667-674 (1992); Hayashimoto, Plant Physiol. 93:857-863 (1990); and Datta et al., Bio-technology 8:736-740 (1990). Such regeneration techniques are described generally in Klee et al., Ann. Rev. Plant Phys. 38:467-486 (1987).

The development or regeneration of transgenic plants containing the exogenous polynucleic acid molecule that encodes a polypeptide of interest is well known in the art. Preferably, the regenerated plants are self-pollinated to provide homozygous transgenic plants, as discussed above. Otherwise, pollen obtained from the regenerated plants is crossed to seed-grown plants of agronomically important lines. Conversely, pollen from plants of these important lines is used to pollinate regenerated plants.

Disease Resistant Soybean Plants and Germplasms

The present invention provides disease resistant soybean plants and germplasms. A Disease resistant soybean plant or germplasm may be produced by any method whereby an R-gene is introduced into the soybean plant or germplasm, including, but not limited to, transformation, protoplast transformation or fusion, a double haploid technique, embryo rescue, gene editing and/or by any other nucleic acid transfer system.

In some embodiments, the soybean plant or germplasm comprises a non-naturally occurring variety of soybean. In some embodiments, the soybean plant or germplasm is at least about 50%, 55%, 60%, 65%, 70%, 75%, 80%, 85%, 90%, 95%, 97%, 99% or 100% identical to that of an elite variety of soybean.

The disease resistant soybean plant or germplasm may be the progeny of a cross between an elite variety of soybean and a variety of soybean that comprises an R-gene for enhanced Disease tolerance (e.g. ASR) wherein the R-gene is selected from the group consisting of genes encoding a protein having a TIR R-gene motif or a gene having between 70-100% homology to any of SEQ ID NOs: 7, 8, 11, or 12 while providing ASR resistance in the plant. In many examples, alternative embodiments will have at least one of at least 90%, 91%, 92%, 93%, 94%, 95%, 96%, 97%, 98%, or 99% homology to any of SEQ ID NOs: 7, 8, 11, or 12.

The disease resistant soybean plant or germplasm may be the progeny of an introgression wherein the recurrent parent is an elite variety of soybean and the donor comprises an R-gene associated with enhanced disease tolerance and/or resistance wherein the donor carries a TIR R-gene motif or a gene having between 70-100% homology to any of SEQ ID NOs: 7, 8, 11, or 12.

The disease resistant soybean plant or germplasm may be the progeny of a cross between a first elite variety of soybean (e.g., a tester line) and the progeny of a cross between a second elite variety of soybean (e.g., a recurrent parent) and a variety of soybean that comprises an R-gene.

A disease resistant soybean plant and germplasm of the present invention may comprise one or more R-genes of the present invention (e.g. any of SEQ ID NOs: 7, 8, 11, or 12).

Disease Resistant Soybean Seeds

The present invention provides disease resistant soybean seeds. As discussed above, the methods of the present invention may be utilized to identify, produce and/or select a disease resistant soybean seed. In addition to the methods described above, a disease resistant soybean seed may be produced by any method whereby an R-gene is introduced into the soybean seed, including, but not limited to, transformation, protoplast transformation or fusion, a double haploid technique, embryo rescue, genetic editing (e.g. CRISPR or TALEN or MegaNucleases) and/or by any other nucleic acid transfer system.

In some embodiments, the disease resistant soybean seed comprises a non-naturally occurring variety of soybean. In some embodiments, the soybean seed is at least about 50%, 55%, 60%, 65%, 70%, 75%, 80%, 85%, 90%, 95%, 97%, 99% or 100% identical to that of an elite variety of soybean.

The disease resistant soybean seed may be produced by a disease resistant soybean plant identified, produced or selected by the methods of the present invention.

A disease resistant soybean seed of the present invention may comprise, be selected by or produced by use of one or more R-genes of the present invention.

EXAMPLES

The following examples are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

Example 1 Identification of ASR Resistant Wild *Glycine* Lines

Multiple wild glycine (*Glycine* canescens, *Glycine clandestina, Glycine tomentella*) lines were evaluated for ASR resistance against sixteen rust strains collected across a diverse range of environments. The rust data were generated using single pustule derived isolates from USDA-ARS (FL Q09, FL Q12, LABR13, FLQ11) and field populations (FL Q15, NC06, Vero, GLC15, UBL, BR south and BR central. The screening was carried out in contained facilities.

Each wild glycine line was evaluated over a multiple day course of infection and rated at various time points. Each accession was screened >2 times with ~4 plants each time in North & South America using a large diverse panel of rust isolates.

Of the wild glycine lines screened for ASR resistance, the following lines showed broad resistance against all ASR strains tested: P1440935, P1483193, P1595799, P1339656, and P1509501.

Example 2 Allele Mining & Associations to P1440935, P1483193, P1595799, P1339656, or P1509501 ASR Loci A resistant parent line was crossed to a susceptible line of the same species (i.e. *G. canescens*×*G. canescens* and *G.* clandestina×G. clandestina) and an F1 plant was generated (See Table 5). The F1 plant was self-fertilized and F2 seed was harvested from the selfed F1 plant. Around 200 F2 seeds were sown and leaf tissue from each plant was collected for DNA preparations and then the plants were inoculated with *Phakopsora pachyrhizi* to determine the resistance/susceptible phenotype of each F2 individual. Tissue from 50 resistant F2s and 50 susceptible F2s were combined in separate pools and genomic DNA was prepared from each pool. Illumina sequencing libraries were prepared from DNA for each of the pools and each library was sequenced in two Illumina HiSeq2000 2×100 bp Paired-End (PE) lanes. The average yield per sample was 383 million read pairs, which equals 77 gigabases of sequence per library. The sequencing reads were trimmed to remove bases with PHRED quality scores of <15.

Quality trimmed reads were aligned to the P1440935 and P1595799 reference genome sequences for *G. canescens* and to the P1339656 reference genome for *G. clandestina* using GSNAP (WU and NACU 2010) as paired-end fragments. If a pair of reads could not be aligned together, they were treated as singletons for alignment. Reads were used in subsequent analyses if they mapped uniquely to the reference (2 mismatches every 36 bp and less than 5 bases for every 75 bp as tails).

SNPs were filtered prior to Bulk segregation analysis (BSA) based on read depth, with SNPs having between 40 and 200× read depth being retained. A Chi-square test was used to select SNPs with significantly different read counts between the two alleles in the two pools. An empirical Bayesian approach (LIU et al. 2012) was used to estimate the conditional probability that there is no recombination between each SNP marker and the causal locus in both the resistant pool and in the susceptible pool. The probability of the linkage between the SNP and the causal gene is the geometric mean of these two conditional probabilities. Around 1000 SNPs were found to have possible linkage to the target locus. A subset of these putatively linked SNPs was used to fine map the locus using phenotyped F2 individuals. See references: LIU, S., C.-T. YEH, H. M. TANG, D. NETTLETON AND P. S. SCHNABLE, 2012 Gene Mapping via Bulked Segregant RNA-Seq (BSR-Seq). PLoS ONE 7: e36406 & Wu, T. D., and S. Nacu, 2010 Fast and SNP-tolerant detection of complex variants and splicing in short reads. Bioinformatics 26: 873-881.

TABLE 5

Plant Crossings & Study Type

| Species | PI# (male) | PI # (female | Study Type | F2: Resistant to Susceptible Ratio |
|---|---|---|---|---|
| *G. canescens* | PI 440935 | PI 505154 | BSA | 3:1 |
| *G. canescens* | PI 440935 | PI 505154 | Indexing | 3:1 |
| *G. canescens* | PI 483193 | PI 505154 | BSR + DEG | 3:1 |
| *G. canescens* | PI 595799 | PI 505154 | Indexing | 3:1 |
| *G. clandestina* | PI 339656 | PI 446943 | BSA | 3:1 |

1. PI440935 Data2Bio LLC (Ames, Iowa) Lab Methodology for gBSA-Seq Analysis for Tetraploid Soybean.

Chromosome discovery for causal loci in the tetraploid soybean population, PI440935 was carried out using Data2Bio's Genomic Bulked Segregant Analysis (gBSA) technology. It was theorized that resistance is controlled by a single dominant gene. Data2Bio generated several libraries from DNA samples extracted from two susceptible tissue pools and two resistant tissue pools and sequenced these in eight (8) Illumina HiSeq2000 2×100 bp Paired-End (PE) lanes. A summary of the reference genomes used for subsequent analyses, read processing from raw data to quality trimming, alignment, SNP discovery and SNP impact are demonstrated in FIGS. 11-13. After various filtering steps 1,099,754 and 324,931 informative SNPs were identified in the PI440935 genome. A Bayesian approach was then used to calculate trait-associated probabilities. Next, physical maps of trait-associated SNPs (probability cutoff 0.01) for the top contigs were created (FIGS. 13-15). One scaffold, scaffold 000056F, was identified and mapped to chromosome 14 of PI440953 (SEQ ID NOs: 1). SNPs from this enriched scaffold were mapped to the public *G. max* genome. An additional smaller cluster of SNPs from other scaffolds were also observed on chromosome 6 (see FIGS. 11-12).

2. PI595799 Data2Bio LLC (Ames, Iowa) Lab Methodology for gBSA-Seq Analysis for Tetraploid Soybean Chromosome discovery for causal loci in the tetraploid soybean population, PI595799 was carried out. A physical map of trait-associated SNPs on contigs was created. The clustering of these SNPs indicates that the resistance gene is located on or near scaffold 000090F (SEQ ID NO: 2). The context sequences associated with these SNPs were also aligned to the public *G. max* genome to create a chromosome-level understanding of the mapping interval. The chromosomal positions of the trait-associated SNPs were then displayed graphically.

3. PI339656 Data2Bio LLC (Ames, Iowa) Lab Methodology for gBSA-Seq Analysis for Tetraploid Soybean.

Chromosome discovery for causal loci in the tetraploid soybean population, PI339656 was carried out using Data2Bio's Genomic Bulked Segregant Analysis (gBSA) technology. It was theorized that resistance is controlled by a single dominant allele. Data2Bio generated several libraries from DNA samples extracted from two susceptible tissue pools and two resistant tissue pools and sequenced these in eight (8) Illumina HiSeq2000 2×100 bp Paired-End (PE) lanes. A summary of the reference genomes used for subsequent analyses, read processing from raw data to quality trimming, alignment, SNP discovery and SNP impact are demonstrated in FIGS. 4-6. After various filtering steps 4,610,234 informative SNPs were identified in the PI339656 genome. A Bayesian approach was then used to calculate trait-associated probabilities. Next, physical maps of trait-associated SNPs (probability cutoff 0.01) for the top contigs were created (FIGS. 13-15). One scaffold, scaffold 14851, was identified and mapped to chromosome 14 of PI339656 (SEQ ID NO: 1). SNPs from this enriched scaffold were mapped to the public *G. max* genome. The data suggest that the causative R gene may map within or near the interval from 3.18 to 3.5 MB on chromosome 14.

Example 3 Embryo Rescue & Introgression of R Gene Intervals into *Glycine max* Lines Embryo rescue is performed and chemical treatment is applied in order to generate amphidiploid shoots. If the amphidiploid plants are fertile they will be used to backcross with *G. max*. Backcrossing with *G. max* and subsequent embryo rescue will need to be performed for several generations in order to gradually eliminate the perennial wild glycine chromosomes.

Wide crosses: Elite Syngenta soybean lines (RM 3.7 to 4.8) were used as the females (pollen recipients) and multiple accessions of *Glycine canescens, G. clandestina*, and *G. tomentella* were used as the males or pollen donors.

Selecting flowers from the glycine plant containing anthers at the proper developmental stage is important. New, fully-opened, brightly colored flowers hold anthers with mature pollen. The pollen should appear as loose, yellow dust. These flowers are removed from the glycine plant and taken to the soybean plant for pollination. Pollen from the *Glycine* plants should be used within 30 minutes of flower removal. It is also important to identify and select soybean flower buds that are ready for pollination. A soybean flower bud is generally ready when it is larger in size when compared to an immature bud. The sepals of the soybean blossoms are lighter in color and the petals are just beginning to appear. First, use a pair of fine-tipped tweezers to carefully detach the sepals from the flower bud to expose the outer set of petals. Then gently grasp and remove the petals (5 in total) from the flower exposing the ring of stamens surrounding the pistil. Since the stigma is receptive to pollen 1 day before the anthers begin shedding pollen it is important to recognize the stage development of "female ready, male not ready". When pollinating soybean flowers at this developmental stage it is not necessary to emasculate the female flower. Locate the stigma on the soybean flower. Then using 1 male flower, carefully peel off the petals to expose the anthers and gently dust the pollen grains onto the stigma of the soybean flower. Care should be taken not to damage the stigma at any time during this process. Starting the day after pollination a hormone mixture is sprayed onto the pollinated flower and eventual developing F1 pod 1× every day until harvest. The pollinated flower or pod is saturated with a light mist of the hormone mixture, taking care not to cause the flower/pod to prematurely detach from the plant. The mixture contains 100 mg GA3, 25 mg NAA and 5 mg kinetin/L distilled water. These hormones aid in the retention of the developing pod and in increased pod growth.

Harvest: Pods from wide crosses are harvested at approximately 14 to 16 days post pollination. (Harvest dates in the literature suggest 19 to 21 days.) Before selecting an individual pod to harvest verify that the sepals were removed (this indicates a wide cross attempt) and that the seed size is as expected for a wide cross. Pods are collected and counted according to wide cross combination to determine crossing success. The average crossing success across multiple soybean females and 5 different accessions of *Glycine canescens* is approximately 40%. The wide cross pods can contain 1 to 3 seeds but generally 2 seeds are found in each F1 pod.

Embryo rescue: Harvested pods are collected and brought back to the lab to be sterilized. The pods are first rinsed with 70% EtOH for 2 to 3 minutes and then placed in 10% Clorox bleach for an additional 30 minutes on a platform shaker at approximately 130 RPM. Finally, the pods are rinsed multiple times with sterile water to remove any residual bleach. Embryo isolation can begin immediately following pod sterilization or pods can be stored at 4° C. for up to 24 hours prior to embryo isolation. The sterilized pods are next taken to a laminar flow hood where the embryos can be rescued. Individual pods are placed in a sterile petri dish and opened using a scalpel and forceps. An incision is made along the length of the wide cross pod away from the seed. The pod can then be easily opened to expose the seed. Alternatively, two pair of forceps can be used to separate the pod shell. Carefully remove the seed from the pod and place in a sterile petri dish under the dissection microscope. Very fine forceps are needed to isolate the embryo from the seed. With forceps in one hand, gently hold the side of the seed away from the embryo, with hilum facing up. Use another pair of forceps in the other hand to remove the seed coat from the side of the seed containing the embryo. Peel off the membrane surrounding the embryo and push the embryo up from tis bottom side. Embryos should be past the globular developmental stage and preferably past the early heart developmental stage (middle to late heart stage, cotyledon stage and early maturation stage embryos are desired). Isolated embryos are transferred to embryo rescue medium such as Soy ER1-1. Embryos can be treated to induce chromosome doubling at this time. (See below for chromosome doubling details.) Isolated embryos remain on embryo rescue medium for 21 to 30 days at 24° C. Embryos may remain in the dark for the entire incubation on ER1-1, may begin the incubation in the dark and complete it in the light, or may spend the entire incubation in the light. There is not a callus induction stage in this protocol. Shoots are developed directly from the embryos.

Chromosome doubling treatments: Either colchicine of trifluralin can be used to induce chromosome doubling. Ideally, late heart stage wide cross embryos (or larger) are chemically treated to induce chromosome doubling at any time from immediately following isolation up to 1 week post isolation. The doubling agent can be mixed in either solid or liquid medium and applied for several hours or up to a few days. Trifluralin is used at a concentration of 10-40 uM in either solid or liquid media. Additionally, colchicine is used at a concentration of 0.4-1 mg/ml in either solid or liquid media. Following the chemical treatment the embryos are transferred to fresh embryo rescue medium.

Shoot regeneration: Developing embryos are transferred from rescue medium to germination medium such as Soy ER GSMv2 for approximately 3 to 5 weeks in the light at 24° C. Alternatively, developing embryos may be transferred from rescue medium to elongation medium such as Soy E1 0 No TCV for approximately 3 to 5 weeks in the light at 24° C. Developing shoots may be transferred from media plates to Phytocons containing either germination or elongation medium for further shoot development. Established shoots are moved to soil. Initial plant care is critical for survival of these shoots.

Ploidy Analysis: Ploidy analysis is conducted using a flow cytometer. Leaf tissue for ploidy analysis is collected from small shoots either in culture or after establishment in soil. Tissue is collected on dry ice and stored at −80° C. until analysis, or collected on wet ice and analyzed the same day. A sample size of 0.5 $cm^2$ is sufficient. Samples are prepared according to the instructions in the Sysmex kit. Each sample set contains an untreated F1 plant (not treated to induce chromosome doubling) as a control. The following are method notes: Wide crosses—Our wide cross success rate is significantly higher than that reported in the literature. No emasculation of female flowers is performed, which saves time and reduces risk of damage to the stigma.

Harvest—Pod harvest at 14 to 16 days after pollination (~5 days earlier than literature, reducing timeline)

Embryo rescue—Our embryo rescue protocol involves direct shoot regeneration from embryos, rather than regeneration through embryogenesis, thus making plant recovery quicker (shoot recovery in approximately 2-3 months, compared to reported up to 1 year timeline). Our protocol does not include culture in the dark following transfer to germination medium. Our protocol does not require a transfer to rooting medium.

Chromosome doubling—Have successfully used trifluralin treatment to produce doubled F1 plant: trifluralin treatment can be done immediately following embryo rescue.

Example 4 ASR Resistance Trait Introgression

Amphidiploid lines generated from the wide cross (i.e. *Glycine canescens* or *Glycine clandestina* crossed with

*Glycine max*) followed by embryo rescue as described in Example 3 were backcrossed multiple times with a recurrent elite *Glycine max* lines. It is known in the art that multiple backcrosses are needed to generate fertile hybrid lines, in particular the literature suggests that a BC3 generation is necessary. In this case it was determined that an additional backcrosses are necessary, e.g. BC4 in the case of *G. tomentella*×*G. max* to generate fertile hybrid plants. F1 hybrid plants produced by the methods as described above were created from wide crosses comprising PI440935, PI483193, PI595799 and PI339656. F1 plants were next crossed as a female with a male recurrent *G. max* plant to perform a first backcross (BC1 progeny). BC1 Progeny were further backcrossed for multiple generations (e.g. BC2). BC plants are evaluated for ASR resistance, chromosome numbers and in some cases lines are genotyped through use of molecular markers as described herein to detect the presence of chromosome intervals corresponding to SEQ ID NOs 1-4 or any marker identified in Tables 1-4.

TABLE 1

Exemplary SNPS from Scaffold 56F

| SNP Name | Position (SEQ ID NO: 1) | Favorable Allele (Rust Resistant) | Unfavorable Allele (Rust Susceptible) |
|---|---|---|---|
| 56F | 3046682 | T | C |
| 56F | 3065127 | T | C |
| 56F | 3131652 | C | T |
| 56F | 3159094 | T | C |
| 56F | 3239763 | T | A |
| 56F | 3265198 | T | A |
| 56F | 3383844 | C | A |
| 56F | 3390809 | T | A |
| 56F | 3404306 | G | C |
| 56F | 3410070 | C | T |
| 56F | 3527033 | A | C |

TABLE 2

Exemplary SNPS from Scaffold 90F

| SNP Name | Position (SEQ ID NO: 1) | Favorable Allele (Rust Resistant) | Unfavorable Allele (Rust Susceptible) |
|---|---|---|---|
| 90F | 33235 | A | T |
| 90F | 33551 | T | G |
| 90F | 33556 | T | G |
| 90F | 33586 | G | T |
| 90F | 33738 | C | T |
| 90F | 34016 | T | A |
| 90F | 34054 | A | G |
| 90F | 34299 | C | A |
| 90F | 34696 | C | A |
| 90F | 35273 | G | T |
| 90F | 37176 | C | T |
| 90F | 37222 | A | T |
| 90F | 37838 | G | C |
| 90F | 37841 | C | T |
| 90F | 37989 | G | T |
| 90F | 38358 | C | T |

TABLE 3

Exemplary SNPS from Scaffold 132FF

| SNP Name | Position (SEQ ID NO: 1) | Favorable Allele (Rust Resistant) | Unfavorable Allele (Rust Susceptible) |
|---|---|---|---|
| 000132F | 1036303 | T | G |
| 000132F | 1066085 | T | C |
| 000132F | 1085690 | G | A |
| 000132F | 1088855 | G | A |
| 000132F | 1090029 | C | T |
| 000132F | 1095842 | G | A |
| 000132F | 1104225 | G | A |
| 000132F | 1105287 | A | G |
| 000132F | 1105896 | C | T |
| 000132F | 1130936 | C | T |
| 000132F | 1131612 | G | T |
| 000132F | 1135444 | A | G |
| 000132F | 1147457 | T | G |
| 000132F | 1148939 | G | A |
| 000132F | 1180730 | G | T |
| 000132F | 1233671 | C | T |
| 000132F | 1253344 | T | C |
| 000132F | 1266772 | G | A |
| 000132F | 1276594 | G | C |
| 000132F | 1282394 | G | A |
| 000132F | 1293582 | G | A |
| 000132F | 1340471 | T | C |
| 000132F | 1420388 | T | C |
| 000132F | 1483043 | C | A |
| 000132F | 1501651 | T | G |
| 000132F | 1504883 | C | A |
| 000132F | 1508972 | C | A |
| 000132F | 1564562 | G | T |
| 000132F | 1589089 | A | G |
| 000132F | 1597852 | T | C |
| 000132F | 1607501 | T | A |
| 000132F | 1615924 | A | G |
| 000132F | 1679827 | A | G |
| 000132F | 1694841 | C | T |
| 000132F | 1731209 | T | G |
| 000132F | 1747932 | G | C |
| 000132F | 1749670 | A | G |
| 000132F | 1775700 | T | C |
| 000132F | 1788283 | A | T |
| 000132F | 1792363 | A | G |
| 000132F | 1801200 | A | G |
| 000132F | 1814495 | T | G |
| 000132F | 1817365 | C | A |
| 000132F | 1820064 | T | C |

TABLE 4

Exemplary SNPS from Scaffold 14851

| SNP Name | Position (SEQ ID NO: 1) | Favorable Allele (Rust Resistant) | Unfavorable Allele (Rust Susceptible) |
|---|---|---|---|
| 14851 | 61341 | T | C |
| 14851 | 61461 | G | T |
| 14851 | 91811 | A | G |
| 14851 | 92509 | A | G |
| 14851 | 92510 | T | A |
| 14851 | 116144 | C | A |
| 14851 | 116271 | G | C |
| 14851 | 116676 | G | T |
| 14851 | 118844 | G | A |
| 14851 | 119667 | A | G |
| 14851 | 119964 | C | A |
| 14851 | 120680 | C | G |
| 14851 | 167877 | T | A |
| 14851 | 168709 | C | T |
| 14851 | 169754 | T | G |
| 14851 | 186158 | T | G |
| 14851 | 188346 | A | G |
| 14851 | 189085 | A | T |
| 14851 | 192255 | G | A |
| 14851 | 195663 | A | C |

TABLE 4-continued

| Exemplary SNPS from Scaffold 14851 | | | |
|---|---|---|---|
| SNP Name | Position (SEQ ID NO: 1) | Favorable Allele (Rust Resistant) | Unfavorable Allele (Rust Susceptible) |
| 14851 | 209847 | C | T |
| 14851 | 211195 | G | A |
| 14851 | 212035 | G | A |
| 14851 | 239552 | G | A |
| 14851 | 240480 | G | T |
| 14851 | 240526 | C | T |
| 14851 | 259531 | C | A |
| 14851 | 260142 | C | G |
| 14851 | 261948 | C | T |
| 14851 | 263314 | G | T |
| 14851 | 298445 | T | C |

The SNPS in table 1-4 are provided by way of illustration only. Additional SNPS for the aforementioned PI lines can be found in US Patent Application Nos. 62/881,035 and 62/881,008, which are herein incorporated by reference.

Example 5 Identification of Two Causative Genes Located within Chromosome 14 Intervals Further genotyping of the various *G. canescens* intervals led to the discovery of two causative genes for ASR resistance located on chromosome 14 within the disclosed intervals. The gene type encodes a TIR R-gene motif and is depicted in SEQ ID NOs 7 and 11 for example. It is contemplated that any of these genes or homologs thereof can be employed in a transgenic, gene editing or breeding method utilizing embryo rescue as described above to generate plants having increased resistance to ASR. Additionally, or optionally, polynucleotide sequences having 70-100% sequence identity to these genes (or to SEQ ID Nos 7 and 11) can be employed in the breeding method to generate the above-described plants.

Example 6 Construction of Vectors Comprising R-Genes and Transformation

Gene components cGcaRG3a-01 (TIR-A) and cGcaRG3b-02 (TIR-B) were stacked together in the native form that includes the exons and introns. However, TIR-B was expressed as an N-terminal truncated form whereby the first 90 nucleotides were removed. The transcription of TIR-A and TIR-B were driven by *Medicago truncatula* promoter and terminator sequences prMt51186-03 & tMt51186-01 and prMt12344-02 & tMt12344-01, respectively. These individual gene cassettes were stacked together in binary vector 24217 (FIG. 1).

Features of vector 24217 are described briefly below.

cGcaRG3b-02 (TIR-B). Start: 2226 End: 3955. A soy rust resistance candidate gene *Glycine canescens* PI595799 encoding a protein containing two Toll/Interleukin-1 receptor (TIR) domains. Version 2 is based on an alternative gene model that is 90 bp shorter than version one. The gene is synthetic to Glyma.14G024500 (Soy_william82_v2)

cGcaRG3a-01 (TIR-A). Start: 7499 End: 10058. A soy rust resistance candidate gene *Glycine canescens* PI595799 encoding a protein containing two Toll/Interleukin-1 receptor (TIR) domains. The gene is synthetic to Glyma.14G024400 (Soy_william82_v2).

cmEPSPSpt-29. Start: 13162 End: 14619. Plastid targeted soybean codon modified class 2 *A. tumefaciens* EPSPS with a T273S modification having a glyphosate tolerance Ki higher than dmEPSPS in vitro.

cSpec-03. Start: 15398 End: 16186. Gene encoding the enzyme aminoglycoside 3'adenyltransferase that confers resistance to spectinomycin and streptomycin for maintenance of the vector in *E. coli* and *Agrobacterium.* cVirG-01. Start: 16486 End: 17211.

cRepA-03. Start: 17241 End: 18314.

bNRB-04. Start: 4 End: 143 (Complementary). Right border region of T-DNA of *Agrobacterium tumefaciens* nopaline ti-plasmid.

bNRB-01-01. Start: 101 End: 125 (Complementary). Right Border Repeat bNLB-05. Start: 14989 End: 15118 (Complementary). Left border region of T-DNA of *Agrobacterium tumefaciens* nopaline ti-plasmid. Differs from bNLB-03 by one base pair to remove ATG start codon for ORF pointing into flanking region.

bNLB-01-01. Start: 15024 End: 15048 (Complementary). 25 bp Left border repeat region of T-DNA of *Agrobacterium tumefaciens* nopaline ti-plasmid.

intron1. Start: 2706 End: 3054.

intron2. Start: 3566 End: 3843.

iMt51186-04. Start: 7217 End: 7467. The first intron of the *Medicago truncatula* gene identified.

iGmEF-02. Start: 12233 End: 13141. The first intron of the soybean elongation factor (EF) gene. iGmEF-01 with an internal BamHI site and a 3' end unintended ORF removed.

xTAG-06. Start: 144 End: 183. 40 bp site for plant insert intactness testing and to stop readthrough ORFs.

xSTOPS-01. Start: 184 End: 195. 6-frame stop to minimize unintended ORF read-through.

Start. Start: 2041 End: 2041. The transcription start site based on cDNA/gDNA alignment.

STOP. Start: 3853 End: 3855.

Start. Start: 7080 End: 7080. Transcription start based on cDNA/gDNA alignment.

Stop. Start: 10364 End: 10364. Transcription stop based on cDNA/gDNA alignment.

xSTOPS-01. Start: 11075 End: 11086. 6-frame stop to minimize unintended ORF read-through.

Start. Start: 12170 End: 12170. Transcription start site.

xSTOPS-01. Start: 14620 End: 14631. 6-frame stop to minimize unintended ORF read-through.

xSTOPS-01. Start: 14929 End: 14940. 6-frame stop to minimize unintended ORF read-through.

xTAG-02. Start: 14941 End: 14980. 40 bp site for plant insert intactness testing and to stop readthrough ORFs.

prMt12344-02. Start: 215 End: 2216. The promoter from the *Medicago truncatula* gene.

prMt51186-03. Start: 4984 End: 7488. A promoter from the *Medicago truncatula* gene; different from prMt51186-01 by one bp substitution (pos2374) to remove an 8mer allergen hit.

prGmEF-05. Start: 11087 End: 13152. Translation elongation factor EF-1 alpha/Tu promoter.

prVirG-01. Start: 16281 End: 16411. virG promoter composed of two promoter elements, one responsive to acetosyringone and phosphate-starvation (bp 45 to 83) and another to medium acidification (86 to 128).

oVS1-02. Start: 18357 End: 18761. Origin of replication and partitioning region from plasmid pVS1 of *Pseudomonas*; serves as origin of replication in *Agrobacterium tumefaciens* host.

oCOLE-06. Start: 19439 End: 20245 (Complementary). The ColE1 origin of replication functional in *E. coli* derived from pUC19.

tMt12344-01. Start: 3962 End: 4968. The terminator based on the *Medicago truncatula* gene.

tMt51186-01. Start: 10068 End: 11067. The terminator based on the *Medicago truncatula* gene.

tNOS-05-01. Start: 14654 End: 14906. Synthetic Nopaline synthetase terminator.

u5GmEF-01. Start: 12170 End: 12232. First 5' UTR of the soybean elongation factor (EF) gene.

u5GmEF-02. Start: 13142 End: 13152. Second 5' UTR of the soybean elongation factor (EF) gene.

xPSlp28-03. Start: 13162 End: 13251. Soybean codon optimized plastid transit peptide derived from the *Chlamydomonas reinhardtii* PSI P28 gene.

Transformation and selection of primary soybean events was achieved using *Agrobacterium* with glyphosate as the selection agent (prGmEF-05: cmEPSPSpt-29: tNOS-05-01).

Taqman analysis of these primary soybean events identified three events harboring both the TIR-A and TIR-B gene cassettes with only two events (GVG00885565; GVG00885566) surviving to maturity (Table 2A).

TABLE 2C

TIR-A Assay

| Name | SEQ ID NO: 26 | SEQ ID NO: 27 | SEQ ID NO: 28 |
|---|---|---|---|
| Oligo Type | PRIMER | PRIMER | PROBE |
| Technology Type | TAQ | TAQ | TAQ |
| Nucleotide Sequence | CATTGG AAGCAT CCAGGA TTTC | TTCAAG GCACCA CGAGGA A | ATCGTTG TTCTCTC CAAAAGC TTCGCG |

TABLE 2A

Summary of Taqman analysis (raw data & copy call) conducted on construct 24217 primary soybean events.

| Plant ID | Pedigree | cm EPSPSpt-29 | cm EPSPSpt-29 | cGcaRG3b-02 + tMt12344-01 | cGcaRG3b-02 + tMt12344-01 | cGcaRG3a-01 | cGcaRG3a-01 |
|---|---|---|---|---|---|---|---|
| GVG00885565 | SYDC181509A001A | 1.25 | 1 | 0.92 | 1 | 6.88 | >2 |
| GVG00885566 | SYDC181501A001A | 0.95 | 1 | 0.84 | 1 | 1.09 | 1 |
| GVG00885564 | SYDC181509A002A | 0.52 | 1 | 0.58 | 1 | 1.04 | 1 |

Tables 2B, 2C, and 2D describe probes and primers usable to determine the presence of TIR-A and TIR-B genes, e.g. in a transformed plant or progeny thereof. In some examples they may further be useful for evaluating introgression of TIR-A or TIR-B genes, e.g. through breeding. Accordingly, the current disclosure is also directed to detecting the novel genes disclosed herein in plants, e.g. soybean.

TABLE 2B

TIR-B Assay

| Name | SEQ ID NO: 23 | SEQ ID NO: 24 | SEQ ID NO: 25 |
|---|---|---|---|
| Oligo Type | PRIMER | PRIMER | PROBE |
| Technology Type | TAQ | TAQ | TAQ |
| Nucleotide Sequence | ACCCTC TCATTG GAATCT CTAAAT ATT | GAGTGT ATCCGT GGCAAG TAAGG | AGACAT AGATGC TCCATA GTTACC GCCCTG |

TABLE 2D

TIR-A Assay

| Name | SEQ ID NO: 29 | SEQ ID NO: 30 | SEQ ID NO: 31 |
|---|---|---|---|
| Oligo Type | PRIMER | PRIMER | PROBE |
| Technology Type | TAQ | TAQ | TAQ |
| Nucleotide Sequence | TGTGTG AGAGAG TTTCTT GCTTGA A | TGCACT GGTTAC GTTTTT CTTTAT CT | CCGTCT TAAAGT AATCAA T |

Example 7 Validation of R-Genes Against ASR

Leaves from primary events GVG00885565 and GVG00885566 were placed in a petri dish on moist paper towel then inoculated with a spore suspension of soybean rusts RTP1 or FLQ12. Leaves from wild type soybean plants served as negative controls. After 14 days, these leaves were evaluated for resistance to soybean rust. As shown in FIG. 2, the leaves from GVG00885565 show clear evidence of resistance to soybean rust RTP1 and FLQ12 compared to the wild type control. The leaves from GVG00885566 show partial resistance.

In order to quantify the level of disease resistance, these leaves were sampled for qRT-PCR analysis to quantify the relative expression of soybean rust β-tubulin gene (FIG. 3).

The results from the qRT-PCR analysis show the level of both RTP1 and FLQQ12 rust β-tubulin expression is dramatically reduced in GVG00885565 compared to the wild type control. The event GVG00885566 has only partial resistance. In the same experiment, the relative expression of the TIR-A and TIR-B genes were determined (FIG. 4). These data show both TIR-A and TIR-B genes are expressed in events GVG00885565 and GVG00885566.

Example 8 Stable Transformation with ASR Candidate Gene Vectors

First generation (T1-generation) seeds from event GVG00885565 were sown in 4 inch pots and grown under greenhouse conditions. These seedlings were sampled for Taqman analysis assays to determine the segregation zygosity (homozygous, heterozygous or null) of each T1 seedling. The qRT-PCR analysis of homozygous and heterozygous plants confirmed expression of both TIR-A and TIR-B has been stably inherited from the primary event to the subsequent generation (FIG. 5).

The homozygous and null seedlings were inoculated with a soybean rust spore suspension from three different populations (RTP1; BRO1—Brazil; BRO3—Brazil). At 14 days post inoculation, these plants were rated for soybean rust disease development. The null plants are completely susceptible to all three rust populations while the TIR-A and TIR-BGVG00885565 homozygous plants have a typical red/brown (RB) resistant lesion type with very little sporulation (FIG. 6).

In this same experiment, the leaves of null and homozygous GVG00885565 seedlings were sample for qRT-PCR analysis to determine the relative expression of soybean rust β-tubulin gene. These data show significantly higher level of soybean rust β-tubulin expression in the null plants at 8, 14 and 21 days post inoculation compared to the TIR-A, TIR-B homozygous plants (FIG. 7).

Example 9. Co-Transformation

Primary soybean events were created via co-transformation with two different *Agrobacterium* strains harboring independent binary vectors for TIR-A (construct 24205; SEQ ID NO: 32) and TIR-B (construct 24192; SEQ ID NO: 33) FIGS. 8A and 8B. These independent constructs express the identical gene cassettes used in the molecular stack of construct 24217. The Taqman analysis of the primary soybean events from the co-transformation experiments identified four events with both TIR-A and TIR-B (Table 3A). Expression of both TIR-A and TIR-B was confirmed by qRT-PCR.

TABLE 3A

Summary of Taqman and qRT-PCR analysis of primary soybean events co-transformed with independent binary vectors 24205 and 24192. Note that the qRT-PCR analysis confirms TIR-A and TIR-B genes are expressed in these primary events.

| | cGcaRG3a-01 | cGcaRG3a-01 | cGcaRG3b-02 | cGcaRG3b-02 | qRT-PDR TIR-A | qRT-PCR TIR-B |
|---|---|---|---|---|---|---|
| GVG01173820 | 0.90 | 1 | 2.02 | 2 | 2.34 | 89.4 |
| GVG01173823 | 0.87 | 1 | 3.30 | >2 | 8.74 | 112.17 |
| GVG01174313 | 0.80 | 1 | 0.68 | 1 | 2.41 | 12.49 |
| GVG01175568 | 1.65 | 2 | 1.83 | 2 | 2.79 | 24.87 |
| GVG01175842 | 0.95 | 1 | 11.67 | >2 | 0.27 | 127.15 |

Two of these primary events GVG01173820 and GVG01173823 were assayed for resistance to different soybean rust populations RTP1, BRO1-Brazil and BRO3-Brazil. Leaves were collected and placed in a petri dish with a moist paper towel. The leaves were inoculated with a soybean rust spore suspension. At 14 days post-inoculation, the leaves were sampled for qRT-PCR analysis of soybean rust β-tubulin gene expression. The results show event GVG01173820 has significantly less β-tubulin gene expression versus all three rust populations while GVG01173823 is most resistant to the Brazil rust populations BRO1 and BRO3 (FIG. 9).

Additional Vector Construction Examples

Additional vector constructs are also provided by way of example.

a) 23891 Vector Construction for R-Gene Comprising *G. clandestina* PI339656-Derived TIR-A and TIR-B SED ID NO: 1 corresponds to Vector 23891. FIG. 10 provides an illustration of vector 23891. Features are described below.

1st TIR-. Start: 1868 End: 3892.

2nd TIR-. Start: 5957 End: 8167.

cNtALS-01. Start: 12147 End: 14141. The NtALS DNA fragment encodes an Acetolactate synthase double mutant (P191A, W568L) from *Nicotiana tabacum.* cSpec-03. Start: 15491 End: 16279. A gene encoding the enzyme aminoglycoside 3'adenyltransferase that confers resistance to spectinomycin and streptomycin for maintenance of the vector in *E. coli* and *Agrobacterium.* cVirG-01. Start: 16579 End: 17304.

cRepA-03. Start: 17334 End: 18407.

bNRB-04. Start: 4 End: 143 (Complementary). Right border region of T-DNA of *Agrobacterium tumefaciens* nopaline ti-plasmid.

bNRB-01-01. Start: 101 End: 125 (Complementary).

bNLB-05. Start: 15082 End: 15211 (Complementary). Left border region of T-DNA of *Agrobacterium tumefaciens* nopaline ti-plasmid. Differs from bNLB-03 by one base pair to remove ATG start codon for ORF pointing into flanking region.

bNLB-01-01. Start: 15117 End: 15141 (Complementary). 25 bp Left border repeat region of T-DNA of *Agrobacterium tumefaciens* nopaline ti-plasmid.

iGmEF-02. Start: 11216 End: 12124. The first intron of the soybean elongation factor (EF) gene. iGmEF-01 with an internal BamHI site and a 3' end unintended ORF removed.

gGcIRG6b-01. Start: 217 End: 4834. A genomic fragment derived from *Glycine clandestina* PI339656 sequence harboring a soy rust resistance gene that encodes a protein containing two Toll Interleukin-like receptor (TIR) domains synthetic to Glyma.14G024500 (Soy_william82_v2).

gGcIRG6a-01. Start: 4842 End: 10050. A genomic fragment derived from *Glycine clandestina* PI339656 sequence harboring a soy rust resistance gene that encodes a protein containing two Toll Interleukin-like receptor (TIR) domains synthetic to Glyma.14G024400 (Soy_william82_v2).

xTAG-06. Start: 144 End: 183.

xSTOPS-01. Start: 184 End: 195.

START. Start: 1868 End: 1870.

STOPS. Start: 3890 End: 3892.

START. Start: 5957 End: 5959.

STOP. Start: 8165 End: 8167.

xSTOPS-01. Start: 10058 End: 10069.

Start. Start: 11153 End: 11153.

xSTOPS-01. Start: 14946 End: 14957.

xSTOPS-01. Start: 15022 End: 15033.

xTAG-02. Start: 15034 End: 15073 promoter. Start: 217 End: 1867.

Promoter. Start: 4842 End: 5956.

prGmEF-02. Start: 10058 End: 12135. Translation elongation factor EF-1 alpha/Tu promoter, including the first intron and neighboring utr, from soybean (williams 82). Like prGmEF-01, but remove internal NcoI, BamHI and SanDI sites, multi-frame stop codons added at the 5' end and one unintended ORF removed at the 3' end.

prVirG-01. Start: 16374 End: 16504.

oVS1-02. Start: 18450 End: 18854.

oCOLE-06. Start: 19532 End: 20338 (Complementary). The ColE1 origin of replication functional in *E. coli* derived from pUC19.

Terminator. Start: 3893 End: 4834.

Terminator. Start: 8168 End: 10050.

tGmEPSPS-02. Start: 14148 End: 14957. Modified version of tGMEPS-01; an EPSPS terminator from *Glycine max.* u5GmEF-01. Start: 11153 End: 11215. 5' UTR of the soybean elongation factor (EF) gene, before intron.

u5GmEF-02. Start: 12125 End: 12135. 5' UTR of the soybean elongation factor (EF) gene, after intron.

The above examples clearly illustrate the advantages of various embodiments of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

---

SEQUENCE LISTING

The patent contains a lengthy sequence listing. A copy of the sequence listing is available in electronic form from the USPTO web site (https://seqdata.uspto.gov/?pageRequest=docDetail&DocID=US12180497B2). An electronic copy of the sequence listing will also be available from the USPTO upon request and payment of the fee set forth in 37 CFR 1.19(b)(3).

---

What is claimed is:

1. A nucleic acid molecule comprising a polynucleotide operably linked to a heterologous promoter, wherein said polynucleotide encodes a polypeptide having at least 95% sequence identity to the full length of SEQ ID NO: 11, wherein co-expression of said polypeptide with a polypeptide having at least 90% sequence identity to the full length of SEQ ID NO: 16, in a soybean plant, enhances resistance of the plant to Asian Soybean Rust (ASR) compared to a control plant.

2. The nucleic acid molecule of claim 1, wherein the polynucleotide comprises:

(a) the nucleotide sequence of any one of SEQ ID NOs: 7, or 8; or (b) a nucleotide sequence having at least 90% sequence identity to the full length of any one of SEQ ID NOS: 7, or 8.

3. The nucleic acid molecule of claim 1, wherein the heterologous promoter is a plant expressible promoter.

4. The nucleic acid molecule of claim 3, wherein the heterologous promoter comprises SEQ ID NO: 9.

5. A vector comprising the nucleic acid molecule of claim 1.

6. A transgenic cell comprising the nucleic acid molecule of claim 1.

7. A method of producing a transgenic soybean plant with increased resistance to a soybean pathogen, the method comprising:

introducing into the genome of a soybean plant, a nucleic acid molecule comprising a first expression cassette comprising a first polynucleotide encoding a polypeptide having at least 95% sequence identity to the full length of SEQ ID NO: 11 operably coupled to a first heterologous, plant active promoter, and a second expression cassette comprising a second polynucleotide encoding a polypeptide having at least 95% sequence identity to the full length of SEQ ID NO: 16 operably coupled to a second heterologous, plant active promoter, wherein the polypeptide having at least 95% sequence identity to the full length of SEQ ID NO: 11 is co-expressed with the polypeptide having at least 95% sequence identity to the full length of SEQ ID NO: 16 in the plant, thereby producing a transgenic soybean plant with increased resistance to a soybean pathogen, wherein the soybean pathogen is Asian Soy Rust.

8. The method according to claim 7, wherein the introducing step comprises:

(i) transforming a soybean plant cell with the nucleic acid molecule, thereby incorporating said nucleic acid molecule into the genome of the soybean plant cell, and regenerating a transgenic soybean plant from the transformed soybean plant cell; or (ii) crossing a first soybean plant comprising the nucleic acid molecule with a second, different soybean plant.

9. The method according to claim 8, wherein the method further comprises obtaining a progeny soybean plant for one or more generations from the transgenic soybean plant, wherein the progeny soybean plant comprises the nucleic acid molecule in the genome of the plant and has increased resistance to the soybean pathogen.

10. A transgenic soybean plant comprising in its genome a first expression cassette comprising a polynucleotide encoding a protein having at least 95% sequence identity to the full length of SEQ ID NO: 11 operably coupled to a first heterologous plant expressible promoter, and a second expression cassette comprising a polynucleotide encoding a protein having at least 95% sequence identity to the full length of SEQ ID NO: 16 operably coupled to a second heterologous plant expressible promoter, wherein said transgenic soybean plant has increased pathogen resistance to Asian Soy Rust (ASR) relative to a soybean plant not comprising the first and second expression cassette.

11. The transgenic soybean plant of claim 10, wherein the soybean plant further has increased resistance to any one of the following: soy cyst nematode, bacterial pustule, root knot nematode, frog eye leaf spot, phytopthora, brown stem rot, nematode, smut, *Golovinomyces cichoracearum, Erysiphe cichoracearum, Blumeria graminis, Podosphaera xanthii, Sphaerotheca fuliginea, Pythium ultimum, Uncinula necator, Mycosphaerella pinodes, Magnaporthe grisea, Bipolaris oryzae, Magnaporthe grisea, Rhizoctonia solani, Phytophthora sojae, Schizaphis graminum, Bemisia tabaci, Rhopalosiphum maidis, Deroceras reticulatum, Diatraea saccharalis, Schizaphis graminum* or *Myzus persicae*.

12. A nucleic acid molecule comprising a polynucleotide operably linked to a heterologous promoter, wherein said polynucleotide encodes a polypeptide having at least 95% sequence identity to the full length of SEQ ID NO: 16, wherein co-expression of said polypeptide, with a polypeptide having at least 95% sequence identity to the full length of SEQ ID NO: 11, in a soybean plant, enhances resistance of the plant to Asian Soybean Rust (ASR) compared to a control plant.

13. The nucleic acid molecule of claim 12, wherein the polynucleotide comprises:
(i) the nucleotide sequence of any one of SEQ ID NOs: 12-13; or
(ii) a nucleotide sequence having at least 90% sequence identity to the full length of any one of SEQ ID NOs: 12-13.

14. A vector comprising the nucleic acid molecule of claim 12.

15. The nucleic acid molecule of claim 1, wherein said polynucleotide encodes a polypeptide having at least 98% sequence identity to the full length of SEQ ID NO: 11.

16. The nucleic acid molecule of claim 1, wherein said polynucleotide encodes a polypeptide having at least 99% sequence identity to the full length of SEQ ID NO: 11.

17. The nucleic acid molecule of claim 16, wherein said polynucleotide encodes a polypeptide comprising SEQ ID NO:11.

18. The nucleic acid molecule of claim 12, wherein said polynucleotide encodes a polypeptide having at least 98% sequence identity to the full length of SEQ ID NO: 16.

19. The nucleic acid molecule of claim 12, wherein said polynucleotide encodes a polypeptide having at least 99% sequence identity to the full length of SEQ ID NO: 16.

20. The nucleic acid molecule of claim 19, wherein said polynucleotide encodes a polypeptide comprising SEQ ID NO: 16.

21. The transgenic soybean plant of claim 10, wherein the polynucleotide in the first expression cassette encodes a protein having at least 98% sequence identity to the full length of SEQ ID NO: 11, and the polynucleotide in the second expression cassette encodes a protein having at least 98% sequence identity to the full length of a SEQ ID NO: 16.

22. The transgenic soybean plant of claim 21, wherein the polynucleotide in the first expression cassette encodes a protein comprising SEQ ID NO: 11, and the polynucleotide in the second expression cassette encodes a protein comprising SEQ ID NO: 16.

23. The transgenic soybean plant of claim 10, wherein the polynucleotide in the first expression cassette comprises SEQ ID NO: 7 or 8, and the polynucleotide in the second expression cassette comprises SEQ ID NO: 12 or 13.

24. The transgenic soybean plant of claim 10, wherein the plant is an elite soybean plant.

25. A seed of a transgenic soybean plant having increased resistance to Asian Soy Rust, wherein the seed comprises, in its genome, a first expression cassette comprising a polynucleotide encoding a protein having at least 95% sequence identity to the full length of SEQ ID NO: 11 operably coupled to a first heterologous plant expressible promoter, and a second expression cassette comprising a polynucleotide encoding a protein having at least 95% sequence identity to the full length of SEQ ID NO: 16 operably coupled to a second heterologous plant expressible promoter.

26. The seed of claim 25, wherein the polynucleotide in the first expression cassette encodes a protein having at least 98% sequence identity to the full length of SEQ ID NO: 11, and the polynucleotide in the second expression cassette encodes a protein having at least 98% sequence identity to the full length of SEQ ID NO: 16.

27. The seed of claim 26, wherein the polynucleotide in the first expression cassette encodes a protein comprising SEQ ID NO: 11, and the polynucleotide in the second expression cassette encodes a protein comprising SEQ ID NO: 16.

28. The seed of claim 25, wherein the polynucleotide in the first expression cassette comprises SEQ ID NO: 7 or 8, and the polynucleotide in the second expression cassette comprises SEQ ID NO: 12 or 13.

29. The seed of claim 25, wherein the transgenic soybean plant is an elite soybean plant.

30. The method of claim 7, wherein the polynucleotide in the first expression cassette encodes a polypeptide having at least 98% sequence identity to the full length of SEQ ID NO: 11, and the polynucleotide in the second expression cassette encodes a polypeptide having at least 98% sequence identity to the full length of SEQ ID NO: 16.

31. The method of claim 30, wherein the polynucleotide in the first expression cassette encodes a polypeptide having at least 99% sequence identity to the full length of SEQ ID NO: 11, and the polynucleotide in the second expression cassette encodes a polypeptide having at least 99% sequence identity to the full length of SEQ ID NO: 16.

32. The method of claim 30, wherein the polynucleotide in the first expression cassette encodes a polypeptide comprising SEQ ID NO: 11, and the polynucleotide in the second expression cassette encodes a polypeptide comprising SEQ ID NO: 16.

33. The nucleic acid molecule of claim 3, wherein the heterologous promoter comprises SEQ ID NO: 14.

34. The nucleic acid molecule of claim 3, wherein the heterologous promoter comprises SEQ ID NO: 19.

35. The nucleic acid molecule of claim 3, wherein the heterologous promoter comprises SEQ ID. NO: 20.

36. The nucleic acid molecule of claim 3, wherein the heterologous promoter comprises SEQ ID NO: 21.

37. The nucleic acid molecule of claim 3, wherein the heterologous promoter comprises SEQ ID NO: 22.

* * * * *